US006489353B2

(12) United States Patent
Karanewsky et al.

(10) Patent No.: US 6,489,353 B2
(45) Date of Patent: *Dec. 3, 2002

(54) C-TERMINAL MODIFIED (N-SUBSTITUTED)-2-INDOLYL DIPEPTIDES AS INHIBITORS OF THE ICE/CED-3 FAMILY OF CYSTEINE PROTEASES

(75) Inventors: Donald S. Karanewsky, Escondido, CA (US); Xu Bai, Carlsbad, CA (US)

(73) Assignee: Idun Pharmaceuticals, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/747,317

(22) Filed: Dec. 20, 2000

(65) Prior Publication Data

US 2002/0025935 A1 Feb. 28, 2002

Related U.S. Application Data

(63) Continuation of application No. 09/345,724, filed on Jun. 30, 1999, now Pat. No. 6,184,244, which is a continuation-in-part of application No. 09/260,816, filed on Mar. 2, 1999, now abandoned, which is a continuation-in-part of application No. 08/928,989, filed on Sep. 12, 1997, now Pat. No. 5,877,197, which is a continuation-in-part of application No. 08/767,175, filed on Dec. 16, 1996, now Pat. No. 5,869,519.

(51) Int. Cl.[7] .................... A61K 31/404; C07D 209/30
(52) U.S. Cl. ........................................ 514/419; 548/492
(58) Field of Search ........................... 548/492; 514/419

(56) References Cited

U.S. PATENT DOCUMENTS

| 5,486,623 A | 1/1996 | Zimmerman et al. | 549/417 |
|---|---|---|---|
| 5,498,616 A | 3/1996 | Mallamo et al. | 514/300 |
| 5,514,694 A | 5/1996 | Powers et al. | 514/357 |
| 5,869,519 A | * 2/1999 | Karanewsky et al. | 514/415 |
| 5,877,197 A | * 3/1999 | Karanewsky et al. | 514/397 |
| 6,184,244 B1 | * 2/2001 | Karanewsky et al. | 514/419 |

FOREIGN PATENT DOCUMENTS

| EP | 0 519 748 A2 | 6/1992 |
|---|---|---|
| EP | 0 623 606 A2 | 4/1994 |
| WO | WO 91/15577 | 10/1991 |
| WO | WO 93/05071 | 3/1993 |
| WO | WO 93/14777 | 8/1993 |
| WO | WO 95/05192 | 2/1995 |
| WO | WO 95/24427 | 9/1995 |
| WO | WO 95/35308 | 12/1995 |
| WO | WO 96/26945 | 9/1996 |
| WO | WO 98/10778 | 3/1998 |
| WO | WO 99/10504 | 3/1999 |
| WO | WO 99/23106 | 5/1999 |
| WO | WO 00/04169 | 1/2000 |

OTHER PUBLICATIONS

Ahmad et al., "Identification and characterization of murine caspse–14, a new member of the caspase family," *Cancer Research* 58: 5201–5205, Nov. 15, 1998.

Cohen, G., "Caspases: the executioners of apoptosis," *Biochemical Journal* 326: 1–16, 1997.

Hu et al., "Caspase–14 is a novel developmentally regulated protease," *Journal of Biological Chemistry* 273(45): 29648–29653, Nov. 6, 1998.

Piérard et al., "Mutant and Chimeric Recombinant Plasminogen Activators. Production in Eukaryotic Cells and Preliminary Characterization," *The Journal of Biological Chemistry* 262(24): 11771–11778, Aug. 25, 1987.

Scaffidi et al., "FLICE is predominantly expressed as two functionally active isoforms, caspase–8/a and caspase–8/b," *The Journal of Biological Chemistry* 272(43):26953–26958, Oct. 24, 1997.

Van de Craen et al., "Identification of a new caspase homologue: caspase–14," *Cell Death and Differentiation* 5(10): 838–848, 1998.

\* cited by examiner

*Primary Examiner*—Laura L. Stockton
(74) *Attorney, Agent, or Firm*—Seed Intellectual Property Law Group PLLC

(57) ABSTRACT

This invention is directed to novel (N-substituted) indole ICE/ced-3-inhibitor compounds. The invention is also directed to pharmaceutical compositions of such indole compounds, plus the use of such compositions in the treatment of patients suffering inflammatory, autoimmune and neurodegenerative diseases, for the prevention of ischemic injury.

41 Claims, No Drawings

C-TERMINAL MODIFIED (N-SUBSTITUTED)-2-INDOLYL DIPEPTIDES AS INHIBITORS OF THE ICE/CED-3 FAMILY OF CYSTEINE PROTEASES

CROSS-REFERENCE TO RELATED APPLICATIONS

This is a continuation of pending U.S. patent application Ser. No. 09/345,724 filed Jun. 30, 1999, now U.S. Pat. No. 6,184,244, which is a continuation-in-part of prior pending U.S. patent application Ser. No. 09/260,816 filed on Mar. 2, 1999, now abandoned, which is a continuation-in-part of U.S. patent application Ser. No. 08/928,989 filed on Sep. 12, 1997, now U.S. Pat. No. 5,877,192, which is a continuation-in-part of U.S. patent application Ser. No. 08/767,175 filed on Dec. 16, 1996, now U.S. Pat. No. 5,869,519.

BACKGROUND OF THE INVENTION

1. Field of the Invention

The present invention relates to novel classes of compounds which are inhibitors of interleukin-1β converting enzyme and related proteases ("ICE/ced-3 family of cysteine proteases"). This invention also relates to pharmaceutical compositions comprising these compounds and to methods of using such pharmaceutical compositions. The compounds, pharmaceutical compositions and methods of this invention are particularly well suited for inhibiting the protease activity of the ICE/ced-3 family and consequently, may be advantageously used as agents against interleukin-1 ("IL-1") mediated diseases, including inflammatory diseases, autoimmune diseases and neurodegenerative diseases and for inhibiting unwanted apoptosis in various disease states such as ischemic injury to the heart (e.g., myocardial infarction), brain (e.g., stroke), and kidney (e.g., ischemic kidney disease).

2. Background Information

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al., *Immunology Today*, 7:45–56 (1986). As such, it is involved in the pathogenesis of chronic and acute inflammatory and autoimmune diseases. IL-1 is predominantly produced by peripheral blood monocytes as part of the inflammatory response. Mosely, B. S. et al., *Proc. Nat. Acad. Sci.*, 84:4572–4576 (1987); Lonnemann, G. et al., *Eur. J. Immunol.*, 19:1531–1536 (1989).

IL-1β is synthesized as a biologically inactive precursor, proIL-1β. ProIL-1β is cleaved by a cysteine protease called interleukin-1β converting enzyme ("ICE") between Asp-116 and Ala-117 to produce the biologically active C-terminal fragment found in human serum and synovial fluid. Sleath, P. R. et al., *J. Biol. Chem.*, 265:14526–14528 (1992); A. D. Howard et al., *J. Immunol.*, 147:2964–2969 (1991).

ICE is a cysteine protease localized primarily in monocytes. In addition to promoting the pro-inflammatory and immunoregulatory properties of IL-1β, ICE, and particularly its homologues, also appear to be involved in the regulation of cell death or apoptosis. Yuan, J. et al., *Cell*, 75:641–652 (1993); Miura, M. et al., *Cell*, 75:653–660 (1993); Nett-Giordalisi, M. A. et al., *J. Cell Biochem.*, 17B:117 (1993). In particular, ICE or ICE/ced-3 homologues are thought to be associated with the regulation of apoptosis in neurogenera-tive diseases, such as Alzheimer's and Parkinson's disease. Marx, J. and M. Baringa, *Science*, 259:760–762 (1993); Gagliardini, V. et al., *Science*, 263:826–828 (1994).

Thus, disease states in which inhibitors of the ICE/ced-3 family of cysteine proteases may be useful as therapeutic agents include: infectious diseases, such as meningitis and salpingitis; septic shock, respiratory diseases; inflammatory conditions, such as arthritis, cholangitis, colitis, encephalitis, endocerolitis, hepatitis, pancreatitis and reperfusion injury, ischemic diseases such as the myocardial infarction, stroke and ischemic kidney disease; immune-based diseases, such as hypersensitivity; auto-immune diseases, such as multiple sclerosis; bone diseases; and certain neurodegenerative diseases, such as Alzheimer's and Parkinson's disease.

ICE/ced-3 inhibitors represent a class of compounds useful for the control of the above-listed disease states. Peptide and peptidyl inhibitors of ICE have been described. However, such inhibitors have been typically characterized by undesirable pharmacologic properties, such as poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92–126. These undesirable properties have hampered their development into effective drugs.

Accordingly, the need exists for compounds that can effectively inhibit the action of the ICE/ced-3 family of proteases, for use as agents for preventing unwanted apoptosis and for treating chronic and acute forms of IL-1 mediated diseases, such as inflammatory, autoimmune or neurodegenerative diseases. The present invention satisfies this need and provide related advantages as well.

SUMMARY OF THE INVENTION

One aspect of the instant invention is the compounds of Formula 1, set forth below.

A further aspect of the instant invention is pharmaceutical compositions comprising a compound of the above Formula 1 and a pharmaceutically-acceptable carrier therefor.

Other aspects of this invention involve a method for treating an autoimmune disease, an inflammatory disease, or a neurodegenerative disease comprising administering an effective amount of a pharmaceutical composition discussed above to a patient in need of such treatment.

Another aspect of the instant invention is a method of preventing ischemic injury to a patient suffering from a disease associated with ischemic injury comprising administering an effective amount of the pharmaceutical composition discussed above to a patient in need of such treatment.

DETAILED DESCRIPTION OF THE INVENTION

The compounds of this invention incorporate an N-substituted indole ring as a peptidomimetic structural fragment. Despite lacking a hydrogen bond donor equivalent to the $P_3$ amide nitrogen of known peptidic inhibitors of ICE, the N-substituted indole compounds of the instant invention have high activity as inhibitors of ICE/ced-3 protease family of enzymes. These compounds also demonstrate other advantages relative to known peptidic inhibitors.

One aspect of the instant invention is the compounds of the Formula 1:

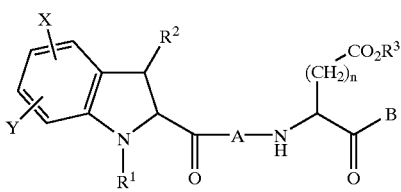

FORMULA 1 wherein:

n is 1 or 2;

R$^1$ is alkyl, cycloalkyl, (cycloalkyl)alkyl, phenyl, (substituted)phenyl, phenylalkyl, (substituted) phenylalkyl, heteroaryl, (heteroaryl)alkyl or $(CH_2)_mCO_2R^4$, wherein m=1–4, and R$^4$ is as defined below;

R$^2$ is a hydrogen atom, chloro, alkyl, cycloalkyl, (cycloalkyl)alkyl, phenyl, (substituted)phenyl, phenylalkyl, (substituted)phenylalkyl, heteroaryl, (heteroaryl)alkyl or $(CH_2)_pCO_2R^5$, wherein p=0–4, and R$^5$ is as defined below;

R$^3$ is a hydrogen atom, alkyl, cycloalkyl, (cycloalkyl) alkyl, phenylalkyl, or (substituted)phenylalkyl;

R$^4$ is a hydrogen atom, alkyl, cycloalkyl, (cycloalkyl) alkyl, phenylalkyl, or (substituted)phenylalkyl;

R$^5$ is a hydrogen atom, alkyl, cycloalkyl, (cycloalkyl) alkyl, phenylalkyl, or (substituted)phenylalkyl;

A is a natural or unnatural amino acid;

B is a hydrogen atom, a deuterium atom, alkyl, cycloalkyl, (cycloalkyl)alkyl, phenyl, (substituted) phenyl, phenylalkyl, (substituted)phenylalkyl, heteroaryl, (heteroaryl)alkyl, halomethyl, $CH_2ZR^6$, $CH_2OCO(aryl)$, or $CH_2OCO(heteroaryl)$, or $CH_2OPO(R^7)R^8$, where Z is an oxygen, OC(=O) or a sulfur atom;

R$^6$ is phenyl, substituted phenyl, phenylalkyl, (substituted phenyl)alkyl, heteroaryl or (heteroaryl)alkyl;

R$^7$ and R$^8$ are independently selected from a group consisting of alkyl, cycloalkyl, phenyl, substituted phenyl, phenylalkyl, (substituted phenyl) alkyl and (cycloalkyl)alkyl; and X and Y are independently selected from the group consisting of a hydrogen atom, halo, trihalomethyl, amino, protected amino, an amino salt, mono-substituted amino, di-substituted amino, carboxy, protected carboxy, a carboxylate salt, hydroxy, protected hydroxy, a salt of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl;

or a pharmaceutically acceptable salt or stereoisomer thereof.

As used in the above formula, the term "alkyl" means a straight or branched $C_1$ to $C_8$ carbon chain such as methyl, ethyl, tert-butyl, iso-propyl, iso-butyl, n-octyl, and the like.

The term "cycloalkyl" means a mono-, bi-, or tricyclic ring that is either fully saturated or partially unsaturated. Examples of such a ring include cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl,1,4-cyclooctadienyl, and the like.

The term "(cycloalkyl)alkyl" means the above-defined alkyl group substituted with one of the above cycloalkyl rings. Examples of such a group include (cyclohexyl) methyl, 3-(cyclopropyl)-n-propyl, 5-(cyclopentyl)hexyl, 6-(adamantyl)hexyl, and the like.

The term "substituted phenyl" specifies a phenyl group substituted with one or more, and preferably one or two, moieties chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, heteroaryl, carboxy, protected carboxy, carboxymethyl, protected carboxymethyl, hydroxymethyl, protected hydroxymethyl, amino, protected amino, (monosubstituted) amino, protected (monosubstituted) amino, (disubstituted)amino, carboxamide, protected carboxamide, N-($C_1$ to $C_6$ alkyl or alkoxy)carboxamide, protected N-($C_1$ to $C_6$ alkyl or alkoxy)carboxamide, N,N-di($C_1$ to $C_6$ alkyl or alkoxy)carboxamide, N-(($C_1$ to $C_6$ alkyl)sulfonyl)amino, N-(phenylsulfonyl)amino or by a substituted or unsubstituted phenyl group, such that in the latter case a biphenyl or naphthyl group results, including biphenyl or naphthyl groups optionally substituted with one or more substituents as identified above.

Examples of the term "substituted phenyl" includes a mono- or di(halo)phenyl group such as 2-, 3- or 4-chlorophenyl, 2,6-dichlorophenyl, 2,5-dichlorophenyl, 3,4-dichlorophenyl, 2-,3- or 4-bromophenyl, 3,4-dibromophenyl, 3-chloro-4-fluorophenyl, 2-, 3- or 4-fluorophenyl and the like, as well as tri- or tetra(halo) phenyl groups such as 2,3,5,6-fluorophenyl; a mono or di(hydroxy)phenyl group such as 2-, 3-, or 4-hydroxyphenyl, 2,4-dihydroxyphenyl, the protected-hydroxy derivatives thereof and the like; a nitrophenyl group such as 2-, 3-, or 4-nitrophenyl; a cyanophenyl group, for example, 2-,3- or 4-cyanophenyl; a mono- or di(alkyl) phenyl group such as 2-, 3-, or 4-methylphenyl, 2,4-dimethylphenyl, 2-, 3- or 4-(isopropyl)phenyl, 2-, 3-, or 4-ethylphenyl, 2-, 3- or 4-(n-propyl)phenyl and the like; a mono or di(alkoxy)phenyl group, for example, 2,6-dimethoxyphenyl, 2-, 3- or 4-(isopropoxy)phenyl, 2-, 3- or 4-(t-butoxy)phenyl, 3-ethoxy-4-methoxyphenyl and the like; 2-, 3- or 4-trifluoromethylphenyl; a mono- or dicarboxyphenyl or (protected carboxy)phenyl group such as 2-, 3- or 4-carboxyphenyl or 2,4-di(protected carboxy)phenyl; a mono- or di(hydroxymethyl)phenyl or (protected hydroxymethyl)phenyl such as 2-, 3- or 4-(protected hydroxymethyl)phenyl or 3,4-di(hydroxymethyl)phenyl; a mono- or di(aminomethyl)phenyl or (protected aminomethyl)phenyl such as 2-, 3- or 4-(aminomethyl) phenyl or 2,4-(protected aminomethyl)phenyl; or a mono- or di(N-(methylsulfonylamino))phenyl such as 2,3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "(substituted phenyl)alkyl" means one of the above substituted phenyl groups attached to one of the above-described alkyl groups. Examples of such groups include 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl, and the like.

The terms "halo" and "halogen" refer to the fluoro, chloro, bromo or iodo groups. There can be one or more halogen, which are the same or different. Preferred halogens are chloro and fluoro.

The term "aryl" refers to aromatic five and six membered carbocyclic rings. Six membered rings are preferred.

The term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms. These five-membered or six-membered rings are fully unsaturated.

The following ring systems are examples of the heterocyclic (whether substituted or unsubstituted) radicals denoted by the term "heteroaryl": thienyl, fluryl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzothiazolyl, benzimidazolyl and indolyl.

Substituents for the above optionally substituted heteroaryl rings are from one to three halo, trihalomethyl, carboxamide, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl groups. Substituents for the heteroaryl group are as heretofore defined, or as set forth below. As used in conjunction with the above substituents for heteroaryl rings, "trihalomethyl" can be trifluoromethyl, trichloromethyl, tribromomethyl or triiodomethyl, "lower alkoxy" means a $C_1$ to $C_4$ alkoxy group, similarly, "lower alkylthio" means a $C_1$ to $C_4$ alkylthio group. The term "substituted alkyl" means the above-defined alkyl group substituted from one to three times by a hydroxy, protected hydroxy, amino, protected amino, cyano, halo, trifluoromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined above substituted with the same groups as listed for a "substituted alkyl" group. The term "(monosubstituted)amino" refers to an amino group with one substituent chosen from the group consisting of phenyl, substituted phenyl, alkyl, substituted alkyl, $C_1$ to $C_7$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted)amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different. The term "heteroaryl(alkyl)" denotes an alkyl group as defined above, substituted at any position by a heteroaryl group, as above defined.

Furthermore, the above optionally substituted five-membered or six-membered heterocyclic rings can optionally be fused to a aromatic 5-membered or 6-membered aryl or heteroaryl ring system. For example, the rings can be optionally fused to an aromatic 5-membered or 6-membered ring system such as a pyridine or a triazole system, and preferably to a benzene ring.

The term "pharmaceutically-acceptable salt" encompasses those salts that form with the carboxylate anions and includes salts formed with the organic and inorganic cations such as those chosen from the alkali and alkaline earth metals, (for example, lithium, sodium, potassium, magnesium, barium and calcium); and ammonium ion; and the organic cations (for example, dibenzylammonium, benzylammonium, 2-hydroxyethylammonium, bis(2-hydroxyethyl)ammonium, phenylethylbenzylammonium, dibenzylethylenediammonium, and like cations.) Other cations encompassed by the above term include the protonated form of procaine, quinine and N-methylglucosamine, the protonated forms of basic amino acids such as glycine, ornithine, histidine, phenylglycine, lysine, and arginine. Furthermore, any zwitterionic form of the instant compounds formed by a carboxylic acid and an amino group is referred to by this term. A preferred cation for the carboxylate anion is the sodium cation. Furthermore, the term includes salts that form by standard acid-base reactions with basic groups (such as amino groups) and includes organic or inorganic acids. Such acids include hydrochloric, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like acids.

The compounds of Formula I may also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include t-butyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxytrityl, 4,4',4"-trimethoxytrityl, 2-phenylpropyl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)-propenyl and like moieties. The species of carboxy-protecting group employed is not critical so long as the derivatized carboxylic acid is stable to the conditions of subsequent reaction(s) and can be removed at the appropriate point without disrupting the remainder of the molecule. Further examples of these groups are found in C. B. Reese and E. Haslam, "Protective Groups in Organic Chemistry," J. G. W. McOmie, Ed., Plenum Press, New York, N.Y., 1973, Chapter 5, respectively, and T. W. Greene and P. G. M. Wuts, "Protective Groups in Organic Synthesis," 2nd ed., John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups bonded to hydroxyl groups, such as the tetrahydropyranyl, 2-methoxyprop-2-yl, 1-ethoxyeth-1-yl, methoxymethyl, β-methoxyethoxymethyl, methylthiomethyl, t-butyl, t-amyl, trityl, 4-methoxytrityl, 4,4'-dimethoxytrityl, 4,4',4"-trimethoxytrityl, benzyl, allyl, trimethylsilyl, (t-butyl)dimethylsilyl, 2,2,2-trichloroethoxycarbonyl, and the like.

Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3. A preferred hydroxy-protecting group is the tert-butyl group. The related term "protected hydroxy" denotes a hydroxy group bonded to one of the above hydroxy-protecting groups.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom.

Examples of such amino-protecting groups include the formyl ("For") group, the trityl group, the phthalimido group, the trichloroacetyl group, the trifluoroacetyl group, the chloroacetyl, bromoacetyl, and iodoacetyl groups, urethane-type protecting groups, such as t-butoxycarbonyl ("Boc"), 2-(4-biphenylyl)propyl-2-oxycarbonyl ("Bpoc"), 2-phenylpropyl-2-oxycarbonyl ("Poc"), 2-(4-xenyl) isopropoxycarbonyl, 1,1-diphenylethyl-1-oxycarbonyl, 1,1-diphenylpropyl-1-oxycarbonyl, 2-(3,5-dimethoxyphenyl)propyl-2-oxycarbonyl ("Ddz"), 2-(p-toluyl)propyl-2-oxycarbonyl, cyclopentanyloxycarbonyl, 1-methylcyclopentanyl-oxycarbonyl, cyclohexanyloxycarbonyl, 1-methyl-cyclohexanyloxycarbonyl, 2-methylcyclohexanyl-oxycarbonyl, 2-(4-toluylsulfonyl) ethoxycarbonyl, 2-(methylsulfonyl)ethoxycarbonyl, 2-(triphenylphosphino)-ethoxycarbonyl, 9-fluorenylmethoxycarbonyl ("Fmoc"), 2-(trimethylsilyl) ethoxycarbonyl, allyloxycarbonyl, 1-(trimethylsilylmethyl) prop-1-enyloxycarbonyl, 5-benzisoxalylmethoxycarbonyl, 4-acetoxybenzyl-oxycarbonyl, 2,2,2-trichloroethoxycarbonyl, 2-ethynyl-2-propoxycarbonyl, cyclopropylmethoxycarbonyl, isobornyloxycarbonyl, 1-piperidyloxycarbonyl, benzyloxycarbonyl ("Cbz"), 4-phenylbenzyloxycarbonyl, 2-methylbenzyloxycarbonyl, α-2,4,5,-tetramethylbenzyl-oxycarbonyl ("Tmz"), 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 4-(decyloxy) benzyloxycarbonyl and the like; the benzoylmethylsulfonyl group, the 2,2,5,7,8-pentamethylchroman-6-sulfonyl group ("PMC"), the dithiasuccinoyl ("Dts") group, the 2-(nitro) phenyl-sulfenyl group ("Nps"), the diphenylphosphine oxide group, and like amino-protecting groups. The species of amino-protecting group employed is not critical so long as the derivatized amino group is stable to the conditions of the subsequent reaction(s) and can be removed at the appropriate point without disrupting the remainder of the molecule. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York, N.Y., 1991, Chapter 7, M. Bodanzsky, "Principles of Peptide Synthesis," 1st and 2nd revised Ed., Springer-Verlag, New York, N.Y., 1984 and 1993, and J. M. Stewart and J. D. Young, "Solid Phase Peptide Synthesis," 2nd Ed., Pierce Chemical Co., Rockford, Ill., 1984, E. Atherton and R. C. Shephard, "Solid Phase Peptide Synthesis—A Practical Approach" IRL Press, Oxford, England (1989), each of which is incorporated herein by reference. The related term "protected amino" defines an amino group substituted with an amino-protecting group discussed above.

The terms "natural and unnatural amino acid" refers to both the naturally occurring amino acids and other non-proteinogenic α-amino acids commonly utilized by those in the peptide chemistry arts when preparing synthetic analogues of naturally occurring peptides, including D and L forms. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of unnatural alpha-amino acids include hydroxylysine, citrulline, kynurenine, (4-aminophenyl) alanine, 3-(2'-naphthyl)alanine, 3-(1'-naphthyl)alanine, methionine sulfone, (t-butyl)alanine, (t-butyl)glycine, 4-hydroxyphenyl-glycine, aminoalanine, phenylglycine, vinylalanine, propargyl-gylcine, 1,2,4-triazolo-3-alanine, thyronine, 6-hydroxytryptophan, 5-hydroxytryptophan, 3-hydroxy-kynurenine, 3-aminotyrosine, trifluoromethylalanine, 2-thienylalanine, (2-(4-pyridyl) ethyl)cysteine, 3,4-dimethoxy-phenylalanine, 3-(2'-thiazolyl)alanine, ibotenic acid, 1-amino-1-cyclopentanecarboxylic acid, 1-amino-1-cyclohexanecarboxylic acid, quisqualic acid, 3-(trifluoromethylphenyl)alanine, (cyclohexyl)glycine, thiohistidine, 3-methoxytyrosine, norleucine, norvaline, alloisoleucine, homoarginine, thioproline, dehydro-proline, hydroxyproline, homoproline, indoline-2-carboxylic acid, 1,2,3,4-tetrahydroisoquinoline-3-carboxylic acid, 1,2,3,4-tetrahydroquinoline-2-carboxylic acid, α-amino-n-butyric acid, cyclohexylalanine, 2-amino-3-phenylbutyric acid, phenylalanine substituted at the ortho, meta, or para position of the phenyl moiety with one or two of the following groups: a ($C_1$ to $C_4$)alkyl, a ($C_1$ to $C_4$)alkoxy, a halogen or a nitro group, or substituted once with a methylenedioxy group; β-2- and 3-thienylalanine; β-2- and 3-furanylalanine; β-2-, 3- and 4-pyridylalanine; β-(benzothienyl-2- and 3-yl)alanine; β-(1- and 2-naphthyl) alanine; O-alkylated derivatives of serine, threonine or tyrosine; S-alkylated cysteine, S-alkylated homocysteine, the O-sulfate, O-phosphate and O-carboxylate esters of tyrosine; 3-(sulfo)tyrosine, 3-(carboxy)tyrosine, 3-(phospho)tyrosine, the 4-methane-sulfonic acid ester of tyrosine, 4-methanephosphonic acid ester of tyrosine, 3,5-diiodotyrosine, 3-nitrotyrosine, ε-alkyllysine, and delta-alkyl ornithine. Any of these α-amino acids may be substituted with a methyl group at the alpha position, a halogen at any position of the aromatic residue on the α-amino side chain, or an appropriate protective group at the O, N, or S atoms of the side chain residues. Appropriate protective groups are discussed above.

Depending on the choice of solvent and other conditions known to the practitioner skilled in the art, compounds of this invention may also take the hemi-ketal, hemi-acetal, ketal or acetal form, which forms are included in the instant invention.

In addition, it should be understood that the equilibrium forms of the compounds of this invention may include tautomeric forms. All such forms of these compounds are expressly included in the present invention.

Also, it will be understood by those skilled in the art that when B in Formula 1 is a hydrogen atom, a semicarbazone may be formed with the resulting aldehyde. Such semicarbazones are also included as compounds of Formula 1, as well as the pharmaceutical compositions containing those compounds. Such semicarbazones also include, for example, semicarbazone derivatives of the optimal groups and embodiments of the 4-oxo-butanoic acid derivatives of the compounds of Formula 1 set forth below.

The compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of exertion. In addition, the compounds may be altered to pro-drug form such that the desired compound is created in the body of the patient as the result of the action of metabolic or other biochemical processes on the pro-drug. Some examples of pro-drug forms include ketal, acetal, oxime, and hydrazone forms of compounds which contain ketone or aldehyde groups, especially where they occur in the group donated as "A" in Formula 1 or the modified aspartic or glutamic residues attached to the group denoted as "A".

In the above Formula 1, a group of optimal compounds occurs when n is one, more so when G is carbonyl group and B is a hydrogen atom, and especially so when $R^3$ is a hydrogen atom or a t-butyl group. Of note within this group of compounds as those when A is naturally-occurring amino acid. This latter group of compounds will be referred to herein as the "4-oxobutanoic compounds".

Within this group of 4-oxobutanoic compounds is a group of optimal compounds wherein $R^1$ is a methyl group, that is, the N-methylindole compounds. One embodiment of this group of N-methylindole compounds occurs when A is an alanine, valine, leucine, phenylalanine, glycine or a proline residue. Compounds of note within each one of these groups of natural amino acid, N-methylindole compounds occur when the N-methylindole is otherwise unsubstituted, that is, wherein X, Y and $R^2$ are each a hydrogen atom, and optimally so when $R^3$ is a hydrogen atom.

Another optimal group of 4-oxobutanoic compounds consists of the N-benzylindole compounds. For example, one group of the N-benzylindole compounds occurs when A is an alanine residue. Of note within this group of alanine compounds are those in which X, Y and $R^2$ are each a hydrogen atom, and especially so where $R^3$ is a hydrogen atom.

An alternate optimal group of 4-oxobutanoic compounds occurs when the N-substituent of the indole group is a 1-butenyl group. An embodiment of this group of N-(1-butenyl)indole compounds occurs when A is a valine residue, and especially so when X, Y and $R^2$ are each a hydrogen atom. An optimal group of this. latter group of compounds occurs when $R^3$ is a hydrogen atom.

Yet another group of optimal 4-oxobutanoic compounds occurs when the N-substituent of the indole ring is a 2'-acetic acid residue. An exemplary group of the N-(2'-acetic acid compounds) occurs when A is an alanine residue. An embodiment of this particular group of alanine compounds occurs when X, Y and $R^2$ are each a hydrogen atom, and especially so when $R^3$ is a hydrogen atom.

A group of the 4-oxobutanoic compounds when the indole group is substituted on the nitrogen with 3'-propionic acid residue is another example of this invention. An optimal group of such N-(propionic acid)indole compounds occurs when A is an alanine residue. Of note within this group of alanine compounds are those when X, Y and $R^2$ are each a hydrogen atom, and especially so when $R^3$ is a hydrogen atom.

Another optimal group of compounds of Formula 1 occurs wherein n is one and more so when B is a monofluoromethyl group. An embodiment of these monofluoromethyl compounds occurs when $R^3$ is a hydrogen atom or a t-butyl group, and an even more so when A is a natural amino acid. An example of these compounds wherein A is a natural amino acid occurs when A is a valine residue. This latter group of valine compounds will be referred to herein as the "4-oxo-5-(fluoropentanoic acid) compounds".

One optimal group of 4-oxo-5-(fluoropentanoic acid) compounds occurs when $R^1$ is a methyl group, in other words, the N-methylindole compounds. An exemplary group of such N-methylindole compounds occurs when $R^2$ is a methyl group and X and Y are each a hydrogen atom, and especially so when $R^3$ is a hydrogen atom. Another exemplary group of such N-methylindole compounds occurs when $R^2$ is a chloro atom and X and Y are each a hydrogen atom, and especially so when $R^3$ is a hydrogen atom. A third exemplary group of N-methylindole compounds occurs when $R^2$ is a chloro group, X is a 5-fluoro group, and Y is a hydrogen atom, and especially so when $R^3$ is a hydrogen atom. A fourth exemplary group of N-methylindole compounds occurs when $R^2$ is iso-butyl and X and Y are each a hydrogen atom, and especially so when $R^3$ is a hydrogen atom.

Another optimal group of 4-oxo-5-(fluoro-pentanoic acid) compounds is composed of N-(3'-phenylprop-1-yl) indole compounds. A group of note within this latter class of compounds occurs when $R^2$, X and Y are each a hydrogen atom, and especially so when $R^3$ is a hydrogen atom.

A third optimal group of 4-oxo-5-(fluoro-pentanoic acid) compounds has an N-(carboxymethyl or protected carboxymethyl) indole moiety. An embodiment of this group occurs wherein $R^2$, X and Y are each a hydrogen atom, and especially so wherein $R^3$ is a hydrogen atom and the nitrogen atom of the indole ring is substituted with a carboxymethyl group.

A fourth optimal group of 4-oxo-5(fluoropentanoic acid) compounds has an N-(homoallyl)indole moiety. One embodiment of note within this group occurs when $R^2$, X and Y are each a hydrogen atom, and especially so when $R^3$ is a hydrogen atom.

Yet another optimal group of compounds of Formula 1 occurs wherein n is one and more so when B is a (2,6-dichorobenzyloxy)-methyl group. An embodiment of these (2,6-dichlorobenzyloxy)methyl compounds occurs when $R^3$ is a hydrogen atom or a t-butyl group, and even more so when A is a natural amino acid. An example of these compounds wherein A is a natural amino acid occurs when A is a valine residue. This latter group of valine compounds will be referred to herein as the "(dichlorobenzyloxy) methyl" compounds.

One optimal group of (dichlorobenzyloxy)methyl compounds occurs when $R^1$ is a methyl group, in other words, the N-methylindole compounds. An exemplary group of such N-methylindole compounds occurs when $R^2$ is a methyl group and X and Y are each a hydrogen atom, and especially so when $R^3$ is a hydrogen atom.

Another optimal group of compounds of Formula 1 occurs wherein n is one and more so when B is a group of the formula $CH_2OPO(R^7)R^8$. An embodiment of these phosphinyloxy-substituted compounds occurs when $R^3$ is a hydrogen atom or a t-butyl group, and an even more so when A is a natural amino acid. An example of these compounds wherein A is a natural amino acid occurs when A is a valine residue. This latter group of valine compounds will be referred to herein as the "phosphinyloxymethyl" compounds.

One optimal group of phosphinyloxymethyl compounds occurs when $R^7$ and $R^8$ are each a phenyl group, and more so when $R^1$ is a methyl group, in other words, the N-methylindole compounds. An exemplary group of such N-methylindole compounds occurs when $R^2$ is a methyl group and X and Y are each a hydrogen atom, and especially so when $R^3$ is a hydrogen atom.

Still another optimal group of compounds of Formula 1 occurs wherein n is one and more so when B is a group $CH_2ZR^6$. Optimal embodiment further occurs when $R^6$ is a heteroaryl group, and more so when Z in an oxygen atom. An embodiment of these (heteroaryl) oxymethyl compounds occurs when $R^3$ is a hydrogen atom or a t-butyl group, and an even more so when A is a natural amino acid. An example of these compounds wherein A is a natural amino acid occurs when A is a valine residue. This latter group of valine compounds will be referred to herein as the "heteroaryloxy" compounds.

One optimal group of heteroaryloxy compounds occurs when the heteroaryloxy group is substituted or unsubstituted pyrazol-5-yloxymethyl, and especially so when this group is (1-phenyl-3-(trifluoromethyl)pyrazol-5-yl)oxymethyl, and even more so when $R^1$ is a methyl group, in other words, the N-methyliindole compounds. An exemplary group of such N-methylindole compounds occurs when $R^2$ is a methyl group and X and Y are each a hydrogen atom, and especially so when $R^3$ is a hydrogen atom.

Another optimal group of compounds of Formula 1 occurs when B is $CH_2ZR^6$ and Z is oxygen or $OC(=O)$.

The compounds of Formula 1 may be synthesized using conventional techniques as discussed below. Advantageously, these compounds are conveniently synthesized from readily available starting materials.

One synthetic route for synthesizing the instant compounds is set forth in the following Scheme I:

SCHEME 1

PG—A—OH + H₂N—Z
(1)  (2)

STEP A ↓

PG—A—N(H)—Z
(3)

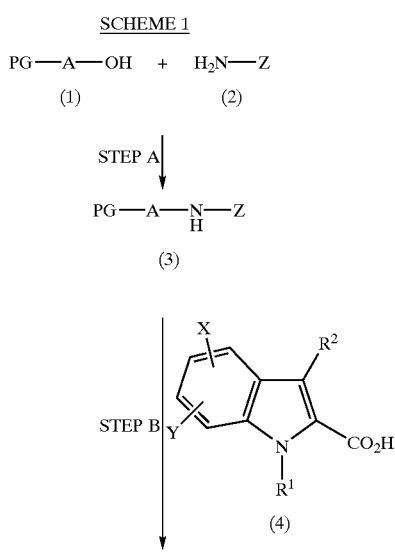

(4)

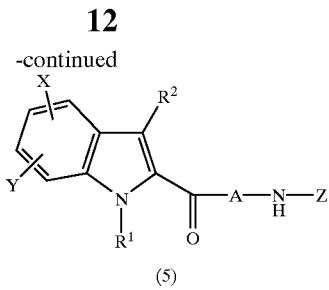

(5)

STEP C ↓

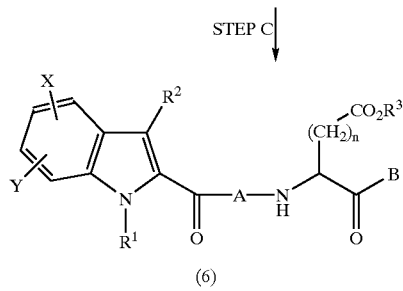

(6)

In the above Scheme I, Formula (2), that is H₂N—Z, is a modified aspartic or glutamic acid residue of Formulas 2a through 2d:

Formula 2a

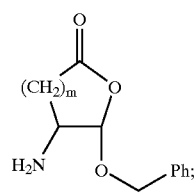

Formula 2b

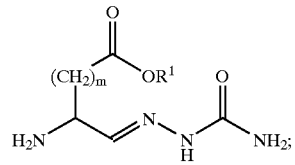

Formula 2c

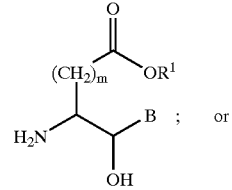

Formula 2d

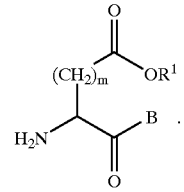

In the above Scheme I, "PG" stands for an amino protecting group and "A" stands for a natural or unnatural amino acid, as discussed above.

The modified aspartic or glutamic acids of Formula 2a–d can be prepared by methods well known in the art. See, for example, European Patent Application 519,748; PCT Patent Application No. PCT/EP92/02472; PCT Patent Application No. PCT/US91/06595; PCT Patent Application No. PCT/US91/02339; European Patent Application No. 623,592;

World Patent Application No. WO 93/09135; PCT Patent Application No. PCT/US94/08868; European Patent Application No. 623,606; European Patent Application No. 618,223; European Patent Application No. 533,226; European Patent Application No. 528,487; European Patent Application No. 618,233; PCT Patent Application No. PCT/EP92/02472; World Patent Application No. WO 93/09135; PCT Patent Application No. PCT/US93/03589; and PCT Patent Application No. PCT/US93/00481, all of which are herein incorporated by reference.

The coupling reactions carried out under Step A are performed in the presence of a standard peptide coupling agent such as the combination of the combination of dicyclohexylcarbodiimide(DCC) and 1-hydroxy-benzotriazole(HOBt), as well as the BOP (benzotriazolyloxy-trio-(dimethylamino)phosphonium hexafluorophosphate) reagent, pyBOP (benzotriazolyloxy-tris(N-pyrolidinyl)phosphoniumhexafluorophosphate), HBTU (O-benzotriazolyly-tetramethylisouronium-hexafluorophosphate), and EEDQ (1-ethyloxycarbonyl-2-ethyloxy-1,2-dihydroquinoline) reagents, the combination of 1-ethyl(3,3'-dimethyl-1-1'-aminopropyl)carbodiimide (EDAC) and HOBt, and the like, as discussed in J. Jones, "Amino Acid and Peptide Synthesis," Steven G. Davis ed., Oxford University Press, Oxford, pp. 25–41 (1992); M. Bodanzky, "Principles of Peptide Synthesis," Hafner et al. ed., Springer-Verlag, Berlin Heidelberg, pp. 9–52 and pp. 202–251 (1984); M. Bodanzky, "Peptide Chemistry, A Practical Textbook," Springer-Verlag, Berlin Heidelberg, pp. 55–73 and pp. 129–180; and Stewart and Young, "Solid Phase Peptide Synthesis," Pierce Chemical Company, (1984), all of which are herein incorporated by reference. The amino protecting group is then removed and the resulting amine is coupled to the 2-(carboxy)indole of Formula 4 (Step B). Again, this coupling reaction uses the standard peptide coupling reactions mentioned above. The indole ring of Formula 4 can be substituted before the reaction in Step B or afterwards. The synthesis and substitution reactions of such an indole ring is well known, as is described, for example, in Brown, R. T. and Joule, J. A. in "Heterocyclic chemistry (ed. P. G. Sammes) (Vol 4 of Comprehensive Organic Chemistry, ed. D. Barton and W. D. Ollis), (1979), Pergamon Press, Oxford; Houlihan, W. J., (ed.) in "Indoles (The Chemistry of Heterocyclic Compounds [ed. A. Weissburger and E. C. Taylor], Vol. 25, Parts 1–3), Wiley Interscience, New York (1972); and Saxton, J. E. (ed.) in "Indoles (The Chemistry of Heterocyclic Compounds)," [ed. A. Weissburger and E. C. Taylor], Vol. 25, Part 4), Wiley Interscience, New York, (1979); all of which are incorporated herewith by reference.

In the case where the coupling reaction was carried out with the amino alcohol of Formula 2c, the alcohol moiety must be oxidized to the corresponding carbonyl compound prior to removal of the protecting groups. Preferred methods for the oxidation reaction include Swern oxidation (oxalyl chloride-dimethyl sulfoxide, methylene chloride at −78° C. followed by triethylamine); and Dess-Martin oxidation (Dess-Martin periodinane, t-butanol, and methylene chloride.) The protecting groups contained in substructures of the Formula 2a–d and A are removed by methods well known in the art. These reactions and removal of some or all of the protecting groups are involved in Step C in the above Scheme.

Pharmaceutical compositions of this invention comprise any of the compounds of Formula 1, of the present invention, and pharmaceutically acceptable salts thereof, with any pharmaceutically acceptable carrier, adjuvant or vehicle (hereinafter collectively referred to as "pharmaceutically-acceptable carriers"). These compositions also include the groups and embodiments of compounds discussed above, as well as the compounds of the Examples discussed below. Pharmaceutically acceptable carriers, adjuvants and vehicles that may be used in the pharmaceutical compositions of this invention include, but are not limited to, ion exchange, alumina, aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethyicellulose, polyarylates, waxes, polyethylene-polyoxypropylene-block polymers, polyethylene glycol and wool fat, and the like.

Such pharmaceutical compositions will be understood to include the optimal groups and embodiments of the compounds of Formula 1 set forth above.

The pharmaceutical compositions of this invention may be administered orally, parenterally, by inhalation spray, topically, rectally, nasally, buccally, vaginally or by an implanted reservoir. Oral and parenteral administration are preferred. The term "parenteral" as used herein includes subcutaneous, intracutaneous, intravenous, intramuscular, intra-articular, intrasynovial, intrastemal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, and aqueous suspensions and solutions. In the case of tablets for oral use, carrier which are commonly used include lactose and corn starch. Lubricating agents, such as magnesium stearate, are also typically added. For oral administration in capsule form useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature. Such materials include, but are not limited to, cocoa butter, beeswax and polyethylene glycols.

Topical administration of the pharmaceutical compositions of this invention is especially useful when the desired treatment involves areas or organs readily accessible to topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-applied transdermal patches are also included in this invention.

The pharmaceutical compositions of this invention may be administered by nasal aerosol or inhalation. Such compositions are prepared according to techniques wel-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The compounds of this invention may be used in combination with either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexons and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical compositions according to this invention may be comprised of a combination of a compound of Formula 1 and another therapeutic or prophylactic agent mentioned above.

The disease states which may be treated or prevented by the instant pharmaceutical compositions include, but are not limited to, inflammatory diseases, autoimmune diseases and neurodegenerative diseases, and for inhibiting unwanted apoptosis involved in ischemic injury, such as ischemic injury to the heart (e.g., myocardial infarction), brain (e.g., stroke), and kidney (e.g., ischemic kidney disease). Methods of administering an effective amount of the above-described pharmaceutical compositions to mammals, also referred to herein as patients, in need of such treatment (that is, those suffering from inflammatory diseases, autoimmune diseases, and neurodegenerative diseases are further aspects of the instant invention.

Another aspect of the instant invention is a method of preventing ischemic injury to a patient suffering from a disease associated with ischemic injury comprising administering an effective amount of the pharmaceutical composition discussed above to a patient in need of such treatment.

Also, each of the methods directed to methods for treating inflammatory diseases, autoimmune diseases, neurodegenerative disease and preventing ischemic injury encompass using any of the optimal groups and embodiments of pharmaceutical compositions set forth above.

Inflammatory disease which may be treated or prevented include, for example, septic shock, septicemia, and adult respiratory distress syndrome. Target autoimmune diseases include, for example, rheumatoid, arthritis, systemic lupus erythematosus, scleroderma, chronic thyroiditis, Graves' disease, autoimmune gastritis, insulin-dependent diabetes mellitus, autoimmune hemolytic anemia, autoimmune neutropenia, thrombocytopenia, chronic active hepatitis, myasthenia gravis and multiple sclerosis. Target neurodegenerative diseases include, for example, amyotrophic lateral sclerosis, Alzheimer's disease, Parkinson's disease, and primary lateral sclerosis. The pharmaceutical compositions of this invention may also be used to promote wound healing. Target diseases associated with harmful, apoptosis, in other words, those associated with ischemic injury, includes myocardial infarction, stroke, and ischemic kidney disease. The pharmaceutical compositions of this invention may also be used to treat infectious diseases, especially those involved with viral infections.

The term "effective amount" refers to dosage levels of the order of from about 0.05 milligrams to about 140 milligrams per kilogram of body weight per day for use in the treatment of the above-indicated conditions (typically about 2.5 milligrams to about 7 grams per patient per day). For example, inflammation may be effectively treated by the administration of from about 0.01 to 50 milligrams of the compound per kilogram of body weight per day (about 0.5 milligrams to about 3.5 grams per patient per day).

The amount of the compounds of Formula 1 that may be combined with the carrier materials to produce a single dosage form will vary depending upon the host treated and the particular mode of administration. For example, a formulation intended for the oral administration of humans may contain from 0.5 milligrams to 5 grams of a compound of Formula 1 combined with an appropriate and convenient amount of a pharmaceutically-acceptable carrier which may vary from about 5 to about 95 percent of the total composition. Dosage unit forms will generally contain between from about 1 milligram to about 500 milligrams of an active compound of Formula 1.

It will be understood, however, that the specific "effective amount" for any particular patient will depend upon a variety of factors including the activity of the specific compound employed, the age, body weight, general health, sex, diet, time of administration, route of administration, rate of excretion, drug combination and the severity of the particular disease undergoing prevention or therapy.

Although this invention focuses on the use of the compounds disclosed herein for preventing and treating IL-1-mediated diseases, the compounds of this invention can also be used as inhibitory agents for other cysteine proteases.

The compounds of this invention are also useful as commercial reagents which effectively bind to the ICE/ced-3 family of cysteine protease or other cysteine proteases. As commercial reagents, the compounds of this invention, and their derivatives, may be used to block proteolysis of a target peptide or may be derivatized to bind to a stable resin as a tethered substrate for affinity chromatography applications. These and other uses which characterize commercial cysteine protease inhibitors will be evident to those of ordinary skill in the art.

The following Examples are intended to illustrate but not limit the present invention.

In the following Examples, proton NMR spectra were obtained at 300 MHz; chemical shifts are quoted downfield from internal tetramethylsilane.

EXAMPLE 1

Assays for Inhibition of ICE/ced-3 Protease Family Activity

A. Determination of $IC_{50}$ Values

Fluorescence enzyme assays detecting the activity of the compounds of Formula 1 utilizing the recombinant ICE and CPP32 enzymes were performed essentially according to Thomberry et al. (*Nature*, 356:768:774 (1992)) and Nicholson et al. (*Nature*, 376:37–43 (1995)) respectively, (herein incorporated by reference) in 96 well microtiter plates. The substrate for these assays was Acetyl-Tyr-Val-Ala-Asp-amino-4-methylcoumarin (AMC) for the ICE assay and Acetyl-Asp-Glu-Val-Asp-amino-4-methylcoumarin for the CPP32 and Mch5 assays. Enzyme reactions were run in ICE buffer (25 mM HEPES, 1 mM EDTA, 0.1% CHAPS, 10% sucrose, pH 7.5) containing 2 mM DTT at room temperature in duplicate. The assays were performed by mixing the following components:

50 µl of either ICE, Mch2, Mch5 or CPP32 (18.8, 38, 8.1 and 0.153 nM concentrations, respectively) enzyme in ICE buffer containing either 8.0 (ICE, Mch2, CPP32) or 20 (Mch5) mM DTT;

50 µl of either the compound of Formula 1 or ICE buffer (control); and

100 µl of 20 µM substrate.

The enzyme and the compound of Formula 1 to be assayed were preincubated in the microtitre plate wells for 30 minutes at room temperature prior to the addition of substrate to initiate the reaction. Fluorescent AMC product formation was monitored for one hour at room temperature by measuring the fluorescence emission at 460 nm using an excitation wavelength of 360 nm. The fluorescence change in duplicate (control) wells were averaged and the mean values were plotted as a function of inhibitor concentration to determine the inhibitor concentration producing 50% inhibition ($IC_{50}$). The reference compound for this assay was Cbz-ValAlaAsp-H, which had an $IC_{50}$ for ICE of 0.064 µM and for CPP32 of 47 µM.

B. Determination of the Dissociation Constant $K_i$ and Irreversible Rate Constant $k_3$ for Irreversible Inhibitors For the irreversible inhibition of a ICE/ced-3 Family Protease enzyme with a competitive irreversible inhibitor; using the model represented by the following formulas:

$$E + 1 \underset{}{\overset{K_i}{\rightleftharpoons}} EI \overset{k_3}{\dashrightarrow} E\text{-}I$$
$$E + S \underset{}{\overset{K_s}{\rightleftharpoons}} ES \overset{k_s}{\dashrightarrow} E + P$$

The product formation at time t may be expressed as:

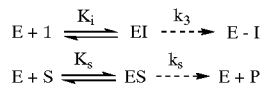

where E, I, EI, and E-I denote the active enzyme, inhibitor, non-covalent enzyme-inhibitor complex and covalent enzyme-inhibitor adduct, respectively. The $K_i$ value is the overall dissociation constant of reversible binding steps, and $k_3$ is the irreversible rate constant. The [S] and $K_S$ values are the substrate concentration and the dissociation constant of the substrate bound to the enzyme, respectively. $[E]^T$ is the total enzyme concentration.

The above equations were used to determine the $K_i$ and $k_3$ values of a given inhibitor bound to a ICE/ced-3 family protease. Thus, a continuous assay was run for sixty minutes at various concentrations of the inhibitor and the substrate. The assay was formulated essentially the same as described in Example 1A above, except that the reaction was initiated by adding the enzyme to the substrate-inhibitor mixture. The $K_i$ and $k_3$ values were obtained by simulating the product AMC formation as a function of time according to Equation 1. The reference compound for this assay was Cbz-ValAlaAsp-$CH_2F$.

EXAMPLE 2

(3S)-3-[(1-Methylindole-2-Carbonyl)Alaninyl] Amino-4-Oxobutanoic Acid, t-Butyl Ester Semicarbazone 1-Methylindole-2-carboxylic acid (107 mg, 0.6 mmol) and (3S)-3-(alaninyl)-amino-4-oxobutanoic acid, t-butyl ester semicarbazone (188 mg, 96%, 0.6 mmol) were dissolved in DMF (2 mL) then both 1-hydroxybenzotriazole-hydrate (96 mg, 0.6 mmol) and 1-(3-dimethylaminopropyl)-3-ethyl carbodiimide hydrochloride (EDAC) (161 mg, 0.84 mmol) was added to the resultant mixture under a nitrogen atmosphere at 0° C. Stirring was continued for 1 hour at 0° C. and an additional 20 hours at room temperature. The reaction mixture was diluted with ethyl acetate, washed successively with saturated aqueous sodium bicarbonate solution and brine, dried over sodium sulfate and concentrated to give a yellow solid. Trituration of the solid with ether afforded the title product as a slightly yellow powder (213 mg, 77%). TLC (methanol/methylene chloride: 1/9, silica gel):$R_f$=0.47; $^1$H-NMR ($CDCl_3$+$CD_3OD$): δ7.96 (d, J=8.0, 1H), 7.57–7.67 (m, 2H), 7.31–7.42 (m, 2H), 7.13–7.19 (m, 2H), 7.06 (s, 1H), 4.91 (m, 1H), 4.65 (q, J=7.1, 1H), 4.01 (s, 3H), 2.59–2.78 (m, J=5.6, 15.7, 2H), 1.49 (d, J=7.1, 3H), 1.39 (s, 9H).

EXAMPLE 3

(3S)-3-[(1-Methylindole-2-Carbonyl)Alaninyl] Amino-4-Oxobutanoic Acid, Semicarbazone (3S)-3-[(1-methylindole-2-carbonyl)alaninyl] amino-4-oxobutanoic acid, t-butyl ester semicarbazone (127 mg, 0.28 mmol) was suspended in anisole (0.2 mL) and methylene chloride (2 mL) and the suspension was treated with trifluroacetic acid (TFA) (1 mL). The resulting solution was stirred for 2 hours under a nitrogen atmosphere at room temperature. The reaction mixture was then concentrated and chased with methylene chloride to give a purple foam. Trituration of the foam with ether gave the title product as a purple powder (108 mg, 97%). TLC (methylene chloride:methanol:acetic acid, 20:1:1, silica gel): $R_f$=0.27; $^1$H-NMR ($CD_3OD$): δ7.62 (d, J=8.10, 1H), 7.44 (d, J=8.2, 1H), 7.24–7.32 (m, 2H), 7.07–7.13 (m, 2H), 4.91 (m, 1H), 4.56 (q, J=7.1, 1H), 3.98 (s, 3H), 2.78 (d, J=6.5, 2H), 1.49 (d, J=7.3, 3H).

EXAMPLE 4

(3S)-3-[(1-Methylindole-2-Carbonyl)Alaninyl] Amino-4-Oxobutanoic Acid (3S)-3-[(1-methylindole-2-carbonyl)alaninyl] amino-4-oxobutanoic acid, semicarbazone (87 mg, 0.22 mmol) was dissolved in methanol (3 mL), formaldehyde (1 mL, 37% wt. aq) and acetic acid (1 mL) and the resultant mixture was stirred for 4 hours under a nitrogen atmosphere at room temperature. The reaction mixture was diluted with water and extracted tw ice with ethyl acetate. The ethyl acetate solution was washed with brine, dried over sodium sulfate and concentrated to give a glassy material which was triturated with ether to afford the title product as a gray powder (24 mg, 32%). TLC (methylene chloride:methanol:acetic acid, 20:1:1, silica gel): $R_f$=0.44; $^1$H-NMR (CD$_3$OD): $\delta$7.62 (d, J=8.0, 1H), 7.44 (dd, J=0.8, 8.4, 1H), 7.26–7.32 (m, 1H), 7.08–7.13 (m, 2H), 4.63–4.53 (m, 2H), 4.31 (m, 1H), 3.99 (s, 3H), 2.48–2.73 (m, 2H), 1.46 (7.1, 3H).

EXAMPLE 5

(3S)-3-(1-Methylindole-2-Carbonyl) Prolinyl] Amino-4-Oxo-Butanoic Acid, t-Butyl Ester Semicarbazone 1-Methylindole-2-carboxylic acid (102 mg, 0.58 mmol) and (3S)-3-(prolinyl)amino-4-oxobutanoic acid, t-butyl ester semicarbazone (189 mg, 0.58 mmol) were dissolved in methylene chloride (2 mL) and DMF (1 mL) and then both 4-dimethylamnino pyridine (DMAP) (71 mg, 0.58 mmol) and EDAC (155 mg, 0.81 mmol) were added to the mixture under a nitrogen atmosphere at 0° C. Stirring was continued for 1 hour at 0° C. and an additional 2 hours at room temperature. The reaction mixture was partitioned between ethyl acetate and 5% KHSO$_4$ solution. The ethyl acetate solution was washed with saturated sodium bicarbonate solution and brine, dried over sodium sulfate and concentrated t o give 153 mg of brown foam. The foam was purified by flash chromatograph on silica gel using 2% methanol-methylene chloride as the eluent to give the title product as a light brown foam (50 mg). TLC: methanol/methylene chloride: 5/95, silica gel): $R_f$=0.27; $^1$H-NMR (CDCl$_3$+CD$_3$OD): $\delta$8.87 (bs, 1H), 7.63 (d, J=7.7, 1H), 7.38–7.50 (m, 2H), 7.17–7.13 (m, 1H), 6.85 (bs, 1H), 4.90–4.81 (m, 2H), 3.92–3.74 (m, 5H), 2.78–1.93 (m, 6H), 1.37 (s, 9H).

EXAMPLE 6

(3S)-3-[(1-Methylindole-2-Carbonyl)Prolinyl] Amino-4-Oxo-Butanoic Acid, Semicarbazone (3S)-3-[(1-Methylindole-2-carbonyl)prolinyl]amino-4-oxobutanoic acid, t-butyl ester semicarbazone (50 mg, 0.1 mmol) was dissolved in anisole (0.2 mL) and methylenechloride (2 mL) and the resultant solution was treated with TFA (1 mL). This reaction mixture was then stirred for 1 hour under a nitrogen atmosphere at room temperature. The reaction mixture was concentrated in vacuo and chased with methylene chloride to give a purple film. The film was triturated with ether to afford the title product as a purple powder (47 mg). TLC: (methylene chloride:methanol:acetic acid, 20:1:1, silica gel): $R_f$=0.18; $^1$H-NMR (CD$_3$OD): $\delta$7.63–6.93 (m, 6H), 6.67 (bs, 1H), 4.89–4.50 (m, 2H), 3.86–3,74 (m, 5H), 2.82–2.74 (m, 2H), 2.40–2.30 (m, 1H), 2.15–1.90 (m, 3H).

EXAMPLE 7

(3S)-3-[(1-Methylindole-2-Carbonyl)Proliny] Amino-4-Oxo-Butanoic Acid (3S)-3-[(1-Methylindole-2-carbonyl)prolinyl] amino-4-oxobutanoic acid, semicarbazone (87 mg, 0.22) mmol) was dissolved in methanol (3 mL), formaldehyde (1 mL, 37% wt. aq) and acetic acid (1 mL) and the resulting mixture was stirred for 4 hours under a nitrogen atmosphere at room temperature. The reaction mixture was concentrated in vacuo, diluted with water, and extracted twice with ethyl acetate. The ethyl acetate solution was washed with brine, dried over sodium sulfate and concentrated to give brown oil (22 mg) which was triturated with ether to afford the title product as a light brown powder (8 mg). TLC (methylene chloride:methanol:acetic acid, 20:1:1, silica gel): $R_f$=0.28; MS for $C_{19}H_{21}N_3O_5$+H$^+$=372; $C_{19}H_{21}N_3O_{5G}$-H$^+$=370).

EXAMPLE 8

(3S)-3-[(1-Methylindole-2-Carbonyl)Valinyl]Amino-4-Oxo-Butanoic acid, t-Butyl Ester Semicarbazone 1-Methylindole-2-carboxylic acid (88 mg, 0.5 mmol) and (3S)-3-(Valinyl)amino-4-oxobutanoic acid, t-butyl ester semicarbazone (163 mg, 0.5 mmol) were dissolved in DMF (1 mL) and methylene chloride (2 mL) then both DMAP (61 mg, 0.50 mmol) and EDAC (134 mg, 0.7 mmol) were added to the solution under a nitrogen atmosphere at 0° C. Stirring was continued for 1 hour at 0° C. and an additional 4 hours at room temperature. The reaction mixture was partitioned between ethyl acetate and 5% KHSO$_4$ solution. The ethyl acetate solution was washed successively with 5% KHSO$_4$ solution, saturated sodium bicarbonate solution and brine solutions, dried over sodium sulfate, and concentrated to give a yellow foam. Trituration of the foam with ether afforded the title product as a slightly yellow powder (203 mg, 86%). TLC (methanol/methylene chloride:5/95, silica gel): $R_f$=0.17.

EXAMPLE 9

(3S)-3-[(1-Methylindole-2-Carbonyl)Valinyl]Amino-4-Oxo-Butanoic Acid Semicarbazone (3S)-3-[(1-Methylindole-2-carbonyl)valinyl] amino-4-oxobutanoic acid, t-butyl ester semicarbazone (170 mg, 0.36 mmol) was dissolved in anisole (0.2 mL) and methylene chloride (2 mL) and the resulting solution was treated with TFA (1 mL). The resulting solution was stirred for 3.5 hours under a nitrogen atmosphere at room temperature. The reaction mixture was concentrated in vacuo and chased with methylene chloride to give a purple foam. Trituration of the foam with ether afforded the title product as a solid purple powder (133 mg, 89%).

EXAMPLE 10

(3S)-3-[1-Methylindole-2-Carbonyl)Valinyl]Amino-4-Oxo-Butanoic Acid (3S)-3-[(1-Methylindole-2-carbonyl)valinyl]amino-4-oxobutanoic acid, semicarbazone (136 mg, 0.33 mmol) was dissolved in methanol (3 mL), formaldehyde (1 mL, 37% wt. aq) and acetic acid (1 mL) and the resulting mixture was stirred for 5 hours under a nitrogen atmosphere at room temperature. The reaction mixture was concentrated in vacuo, diluted with water, and extracted twice with ethyl acetate. The combined ethyl acetate solutions were washed with brine, dried over sodium sulfate and concentrated in vacuo to give a purple foam which was triturated with ether to afford the title product as a purple powder (40 mg, 33%). TLC: (methylene chloride:methanol:acetic acid, 20:1:1, silica gel): $R_f$=0.36; MS for $C_{19}H_{23}N_3O_5$+H$^+$=374; $C_{19}H_{23}N_3O_{5G}$H$^+$=372.

EXAMPLE 11

(3S)-3-[(1-Methylindole-2-Carbonyl)Leucinyl] Amino-4-Oxo-Butanoic Acid, t-Butyl Enter Semicarbazone 1-Methylindole-2-carboxylic acid (70 mg, 0.4 mmol) and 3(S)-(Leucinyl)amino-4-oxobutanoic acid, t-butyl ester semicarbazone (131 mg, 0.4 mmol) were dissolved in methylene chloride (2 mL) and both DMAP (49 mg, 0.40 mmol) and EDAC (107 mg, 0.56 mmol) were added to the solution under a nitrogen atmosphere at 0° C. Stirring was continued for 1 hour at 0° C. and an additional 3 hours at room temperature. The reaction mixture was partitioned between ethyl acetate and 5% $KHSO_4$ solution. The ethyl acetate solution was washed successively with 5% $KHSO_4$ solution, saturated with sodium bicarbonate solution (2×) and brine, dried over sodium sulfate, and concentrated in vacuo to give a crude solid. Trituration of the solid with either afforded the title product as a white powder (156 mg, 80%). TLC (methanol/methylene chloride: 5/95, silica gel): $R_f$=0.42; $^1$H-NMR ($CDCl_3$+$CD_3OD$): δ8.18 (s, 1H), 7.66–7.11 (m, 6H), 6.97 (s, 1H), 6.32 (d, J=7.7, 1H), 4.95–4.88 (m, 1H), 4.70–4.62 (m, 1H), 4.03 (s, 3H), 2.82–2.56 (m, 2H), 1.87–1.58 (m, 3H), 138 (9H), 1.00 (t, J-6.3, 6H).

EXAMPLE 12

(3S)-3-[(1-Methylindole-2-Carbonyl)Leucinyl] Amino-4-Oxo-Butanoic Acid, Semicarbazone (3S)-3-[(1-Methylindole-2-carbonyl)leucinyl]amino-4-oxobutanoic acid, t-butyl ester semicarbazone (132 mg, 0.27 mmol) was dissolved in anisole (0.2 mL) and methylene chloride (2 mL) and the resulting solution was treated with TFA (1 mL). The resulting solution was stirred for 3 hours under a nitrogen atmosphere at room temperature. The reaction mixture was concentrated in vacuo and chased with methylene chloride to give a pink foam. Trituration of the foam with ether afforded the title product as a pink powder (108 mg, 92%). TLC (methylene chloride:methanol:acetic acid, 20:1:1, silica gel): $R_f$=0.22; $^1$H-NMR ($CD_3OD$): δ7.62 (dt, J=8.0, 1.1, 1H), 7.45 (dd, J=8.5, 0.8, 1H), 732–7.23 (m, 2H), 7.13–7.08 (m, 2H), 4.94–4.89 (m, 1H), 4.64–4.59 (m, 1H), 3.98 (s, 3H), 2.78 (d, J=6.2, 2H), 1.82–1.70 (m, 3H), 1.02 (d, J=6.0, 3H), 0.99 (d, J=6.3, 3H).

EXAMPLE 13

(3S)-3-[(1-Methylindole-2-Carbonyl)Leucinyl] Amino-4-Oxo-Butanoic Acid (3S)-3-[(1-Methylindole-2-carbonyl)leucinyl] amino-4-oxobutanoic acid, semicarbazone (90 mg, 0.21 mmol) was dissolved in methanol (3 mL), formaldehyde (1 mL, 37% wt. aq) and acetic acid (1 mL) and the resulting solution was stirred for 7 hours under a nitrogen atmosphere at room temperature. The reaction mixture was concentrated in vacuo, diluted with water, and extracted twice with ethyl acetate. The ethyl acetate solution was washed with brine, dried over sodium sulfate, and concentrated in vacuo to give a purple foam which was triturated with ether to afford the title product as a purple powder (35 mg, 43%). TLC: (methylene chloride:methanol:acetic acid, 20:1:1, silica gel): $R_f$=0.45; MS for $C_{20}H_{25}N_3O_5$; M+H$^+$=388; M−H$^+$=386.

EXAMPLE 14

(3S)-3-[(1-Methylindole-2-Carbonyl)Phenylalaninyl] Amino -4-Oxabutanoic acid, t-Butyl Ester Semicarbazone 1-Methylindole-2-carboxylic acid (72 mg, 0.41 mmol) and 3(S)-(phenylalaninyl]amino-4-oxobutanoic acid, t-butyl ester semicarbazone (154 mg, 0.41 mmol) were dissolved in methylene chloride (2 mL) and both DMAP (53 mg, 0.43 mmol) and EDAC (109 mg, 0.57 mmol) were added to the solution under a nitrogen atmosphere at 0° C. Stirring was continued for 1 hour at 0° C. and an additional 4 hours at room temperature. The reaction mixture was partitioned between ethyl acetate and 5% $KHSO_4$ solution, successively, dried over sodium sulfate, and concentrate to give a white solid. Trituration of the solid with ether afforded the title product as a white powder (179 mg, 82%). TLC (methanol/methylene chloride: 5/95, silica gel): $R_f$=0.44.

EXAMPLE 15

(3S)-3-[(1-Methylindole-2-Carbonyl)Phenylalaninyl] amino -4-Oxobutanoic Acid, Semicarbazone (3S)-3-[(1-Methylindole-2-carbonyl) phenylalaninyl] amino-4-oxobutanoic acid, t-butyl ester semicarbazone (154 mg, 0.30 mmol) was dissolved in anisole (0.2 mL) and methylene chloride (2 mL) and the resulting solution was treated with TFA (1 mL). The resulting solution was stirred for 4 hours under a nitrogen atmosphere at room temperature. The reaction mixture was concentrated in vacuo and azeotroped with methylene chloride to give a purple solid. Trituration of the solid with ether afforded the title product as a purple powder (141 mg, 100%). TLC: (methylene chloride:methanol:acetic acid, 20:1:1, silica gel): $R_f$=0.25.

EXAMPLE 16

(3S)-3-[(1-Methylindole-2-Carbonyl)Phenylalaninyl] Amino-4-Oxobutanoic Acid (3S)-3-[(1-Methylindole-2-carbonyl)phenyl-alaninyl] amino-4-oxobutanoic acid, semicarbazone (116 mg, 0.25 mmol) were dissolved in methanol (3 mL), formaldehyde (1 mL, 37% wt. aq) and acetic acid (1 mL) and the resulting solution was stirred for 9 hours under a nitrogen atmosphere at room temperature. The reaction mixture was concentrated in vacuo, diluted with water, and extracted twice with ethyl acetate. The ethyl acetate solution was washed with brine, dried over sodium sulfate and concentrated to give a crude product which was triturated with ether to afford the title product as a brown powder (26 mg, 25%). TLC (methylene chloride:methanol:acetic acid, 20:1:1, silica gel): $R_f$=0.33; MS for $C_{23}H_{21}N_3O_5$; M+H$^+$=422; M−H$^+$=420.

EXAMPLE 17

(1-Methylindole-2-Carbonyl)Glycine, Methyl Ester

DMAP (1.222 g, 0.01 mol) and EDAC (2.680 g, 0.014 mol) were added as solids to a solution of 1-methylindole-2-carboxylic acid (1.752 g, 0.01 mol) and glycine methyl ester hydrochloride (1.256 g, 0.01 mol) in methylene chloride (30 mL) and DMF (5 mL) under a nitrogen atmosphere at 0° C. Stirring was continued for 1 hour at 0° C. and then for 3 hours at room temperature. The reaction mixture was partitioned with ethyl acetate and 5% $KHSO_4$ solution and the aqueous layer was extracted with ethyl acetate. The combined ethyl acetate solution was washed with 5% $KHSO_4$ solution, saturated sodium bicarbonate solution (2×) solution and brine, dried over sodium sulfate, and concentrated to give a purple powder as crude product. Trituration of the powder with ether afforded the title product (1.734 mg, 70%). TLC (methanol/methylene chloride 1:9): $R_f$=0.61; $^1$H-NMR ($CDCl_3$): δ7.65 (dt, J=8.0, 1.1, 1H), 7.41–7.31 (m, 2H), 7.16 (dd, J=6.6, 1.4, 1H) 6.96 (d, J=0.5, 1H), 6.67 (bs, 1H), 4.25 (d, J=5.2, 2H), 4.05 (s, 3H), 3.82 (s, 3H).

EXAMPLE 18

(1-Methylindole-2-Carbonyl)Glycine (1-Methylindole-2-carbonyl)glycine methyl ester (1.687 g, 6.85 mmol) was dissolved in 1,4-dioxane (10 mL) and was treated with 1 N lithium hydroxide (7.0 mL, aq) with stirring. The reaction mixture turned clear immediately and was acidified with 1N HCl and concentrated to remove 1,4-dioxane to result in a purple precipitate. The precipitate was filtered, washed with water, and dried in vacuo to give the title product as a purple powder (1.482 g, 93%). TLC: (methylene chloride:methanol:acetic acid, 20:1:1 silica gel): $R_f=0.28$; $^1$H-NMR (CD$_3$OD): δ7.61 (dt, J=8.2, 1H). 744 (dd, J=8.5, 0.8, 1H), 7.32–7.26 (m, 1H), 7.13–7.09 (m, 1H), 7.04 (s, 1H), 4.08 (s, 2H), 3.99 (s, 3H).

EXAMPLE 19

(3S)-3-[(1-Methylindole-2-Carbonyl)Glycine] Amino-4-Oxo-Butanoic Acid, t-Butyl Ester Semicarbazone (1-Methylindole-2-carbonyl)glycine (186 mg, 0.8 mmol) was dissolved in methylene chloride (5 mL) and DMF (1 mL) and the resulting solution was treated with 1-hydroxybenzotriazole hydrate (129 mg, 0.84 mmol) and EDAC (215 mg, 1.12 mmol) under a nitrogen atmosphere and the reaction mixture stirred for 10 minutes at 0° C. 3(S)-Amino-4-oxobutanoic acid, t-butyl ester semicarbazone p-toluenesulfate (312 mg, 0.8 mmol) followed by N-methylmorpholine (0.09 mL, 0.8 mmol), were added to the reaction mixture and the mixture was stirred for 1 hour at 0° C. and an additional 4 hours at room temperature. The reaction mixture was partitioned between ethyl acetate and 5% KHSO$_4$, and the product precipitated out during the work-up. The white precipitate from the aqueous portion was obtained by filtration and washing with water and ether. Another portion of white precipitate was obtained by concentration of the organic layer and trituration of the residue with ether. The combined precipitate was the title product (297 mg, 66%). TLC (methanol/methylene chloride: 1/9, silica gel): $R_f=0.42$; $^1$H-NMR (CDCl$_3$) δ7.65 (d, J=8.0, 1H), 7.41–7.34 (m, 2H), 7.19–7.13 (m, 2H), 7.05 (d, J=0.5, 1H), 4.95–4.93 (m, 1H), 4.08 (s, 2H), 4.03 (s, 3H), 2.79–2.59 (m, 2H), 1.41 (s, 9H).

EXAMPLE 20

(3S)-3-[(1-Methylindole-2-Carbonyl)Glycinyl] Amino-4-Oxo-Butanoic Acid, Semicarbazone (3S)-3-[(1-Methylindole-2-carbonyl)glycinyl]amino-4-oxobutanoic acid, t-butyl ester semicarbazone (118 mg, 0.26 was dissolved in anisole (0.2 mL) and methylene chloride (2 mL) and the resulting solution was treated with TFA (1 mL). The resulting solution was stirred for 3 hours under a nitrogen atmosphere at room temperature. The reaction mixture was concentrated in vacuo and chased with methylene chloride to give a green solid. Trituration of the solid with ether afforded the title product as a green powder (88 mg, 87%). TLC: (methylene chloride:methanol:acetic acid, 20:1:1, silica gel): $R_f=0.47$; $^1$H-NMR (CD$_3$OD): δ7.63–7.08 (m, 6H), 4.95 (m, 1H), 4.05 (s, 2H), 4.01 (s, 3H), 3.77 (d, J=5.8, 2H).

EXAMPLE 21

(3S)-3-[(1-Methylindole-2-Carbonyl)Glycinyl]-Amino-4-Oxo-Butanoic Acid (3S)-3-[(1-Methylindole-2-carbonyl)glycinyl] amino-4-oxobutanoic acid, semicarbazone (76 mg, 0.20 mmol) was dissolved in a mixture of methanol (3 mL), formaldehyde (1 mL, 37% wt. aq) and acetic acid (1 mL) and the mixture was stirred for 6 hours under a nitrogen atmosphere at room temperature. The reaction mixture was concentrated in vacuo, diluted with water, extracted twice with ethyl acetate. The combined ethyl acetate solutions were washed with brine, dried over sodium sulfate, and concentrated to give a crude product which was triturated with ether to afford the title product as a light yellow powder (29 mg, 44%). TLC (methylene chloride:methanol:acetic acid, 8:1:1, silica gel): $R_f=0.61$; MS for $C_{16}H_{17}N_3O_5$:M+H$^+$, 330. $^1$H-NMR (CD$_3$OD): δ7.73–7.08 (m, 5H), 4.90–3.8 (m, 7H), 2.72–2.47 (m, 2H).

EXAMPLE 22

(3S)-3-[(1-Benzyiindole-2-Carbonyl)Alaninyl] Amino-4-Oxo-Butanoic Acid, t-Butyl Ester Semicarbazone 1-Benzylindole-2-carboxylic acid (477 mg, 1.9 mmol) and 3(S)-(alaninyl)amino-4-oxobutanoic acid, t-butyl ester semicarbazone (581 mg, 1.9 mmol) were dissolved in methylene chloride (8 mL) and both DMAP (232 mg, 1.9 mmol) and EDAC (498 mg, 2.6 mmol) were added to the solution under a nitrogen atmosphere at 0° C. The resultant solution was stirred for 1 hour at 0° C. and an additional 2 hours at room temperature. The reaction mixture was diluted with ethyl acetate, washed successively with saturated sodium bicarbonate solution and brine, dried over sodium sulfate, and concentrated to give a yellow foam. Flash column chromatographic purification of the foam (silica gel, methanol/methylene chloride 2–5%) afforded the title product as a white powder (570 mg, 56%). TLC (methanol/methylene chloride: 1/9, silica gel): $R_f=0.38$; $^1$H-NMR (CDCl$_3$): δ8.60 (bs, 1H), 7.67 (dd, J=8.0, 1.1, 1H), 7.50 (d, J=8.0, 1H). 7.33–7.01 (m, 8H), 6.79 (d, J=7.4, 1H), 5.78 (s, 2H), 4.87–4.83 (m, 1H), 4.67–4.62 (m, 1H), 2.73–2.43 (m, 2H), 1.46 (d, J=7.1, 3H), 1.39 (s, 9H).

EXAMPLE 23

(3S)-3-[(1-Benzylindole-2-Carbonyl)Alaninyl] Amino-4-Oxo-Butanoic Acid, Semicarbazone (3S)-3-[(1-Benzylindole-2-carbonyl)alaninyl]amino-4-oxobutanoic acid, t-butyl ester semicarbazone (247 mg, 0.46 mmol) was dissolved in anisole (0.5 mL) and methylene chloride (2 mL) and the resultant mixture was treated with TFA (1 mL). The resulting solution was stirred for 3.5 hours under a nitrogen atmosphere at room temperature. The reaction mixture was concentrated and chased with methylene chloride to give a light green solid. Trituration of the solid with ether afforded the title product as a green powder (215 mg, 98%). TLC (methylene chloride:methanol:acetic acid, 8:1:1, silica gel): $R_f=0.50$; $^1$H-NMR (CD$_3$OD): δ8.26 (d, J=8.0, 1H), 7.65 (d, J=8.0, 1H), 7.39 (dd, J=8.5, 0.8, 1H), 7.26–7.01 (m, 8H), 5.79 (d, J=7.4, 2H), 4.56–4.49 (m, 1H), 2.77–2.62 (m, 2H), 1.43 (d, J=7.4, 3H).

EXAMPLE 24

(3S)-3-[(1-Benzylindole-2-Carbonyl)Alaninyl] Amino-4-Oxo-Butanoic Acid (3S)-3-[( -Benzylindole-2-carbonyl)alaninyl] amino-4-oxobutanoic acid, semicarbazone (176 mg, 0.37 mmol) was dissolved in methanol (4.5 mL), formaldehyde (1.5 mL, 37% wt. aq) and acetic acid (1.5 mL) and the resulting mixture was stirred for 4 hours under a nitrogen atmosphere at room temperature. The reaction mixture was concentrated in vacuo, diluted with water, and extracted twice with ethyl acetate. The ethyl acetate solution was washed with brine, dried over sodium sulfate, and concentrated to give a crude product which was triturated with ether to afford the title product as a light green powder (113 mg, 72%). TLC: (methylene chloride:methanol:acetic acid, 20:1:1, silica gel): $R_f$=0.38; MS for $C_{23}H_{23}N_3O_5$; $M+H^+$=422; $M-H^+$420. $^1$H-NMR (CD$_3$OD): δ7.65 (d, J=8.0, 1H), 7.37 (dd, J=8.2, 0.8, 1H), 7.24–7.04 (m, 8H), 5.87–5.73 (m, 2H) 4.60–4.49 (m, 2H), 4.32–4.23 (m, 1H), 2.69–2.44 (m, 2H), 1.41 (d, J=7.1, 2 sets, 3H).

EXAMPLE 25

(3S)-3-(1-(4'-Butenyl)Indole-2-Carbonyl)Valinyl] Amino-4-Oxobutanoic Acid, t-Butyl Ester Semicarbazone

[1-(4'-Butenyl)indole]-2-carboxylic acid (108 mg, 0.5 mmol) and 3(S)-(valinyl)amino-4-oxobutanoic acid, t-butyl ester semicarbazone (163 mg, 0.5 mmol) were dissolved in methylene chloride (3 mL). To this solution was added both DMAP (61 mg, 0.5 mmol) and EDAC (134 mg, 0.7 mmol) under a nitrogen atmosphere at 0° C. and the resultant reaction mixture was stirred for 1 hour at 0° C. and an additional 5 hours at room temperature. The reaction mixture was diluted with ethyl acetate, washed successively with saturated sodium bicarbonate solution and brine, dried under sodium sulfate, and concentrated to give a yellow foam. Trituration of the foam with ether afforded the title product as a slightly yellow powder (146 mg, 55%). TLC methanol/methylene chloride: 1/9, silica gel): $R_f$=0.23; $^1$H-NMR (CDCl$_3$): δ8.69 (bs, 1H), 7.64 (d, J=8.0, 1H) 7.41–7.13 (m, 3H), 6.99 (s, 1H), 6.91 (d, J=8.8, 1H), 5.85–5.71 m, 1H), 5.04–4.94 (m, 3H), 4.65–4.45 (m, 3H), 3.52–2.50 (m, 4H), 2.33–2.26 (m, 1H), 1.41 (s, 9H), 1.05–1.02 (m, 6H).

EXAMPLE 26

(3S)-3-[(1-(4'-Butenyl)Indole-2-Carbonyl)Valinyl] Amino-4-Oxobutanoic Acid, Semicarbazone (3S)-3-[(1-(4'-Butenyl)indole-2-carbonyl) valinyl]amino-4-oxobutanoic acid, t-butyl ester semicarbazone (126 mg, 0.24 mmol) was dissolved in anisole (0.2 mL) and methylene chloride (2 mL) and the resulting solution was treated with TFA (1 mL). The acidified reaction mixture was stirred for 4 hours under a nitrogen atmosphere at room temperature. The reaction mixture was concentrated and chased with methylene chloride to give a crude solid. Trituration of the solid with ether afforded the title product as a purple powder (99 mg, 88%). TLC (methylene chloride:methanol:acetic acid, 20:1:1, silica gel): $R_f$=0.36; $^1$H-NMR (CD$_3$OD): δ8,46 (d, J=8.0, 1H) 8.12 (d, J=8.2, 1H), 7.62 (d, J=8.0, 1H), 7.46 (dd, J=8.5, 0.8, 1H), 7.31–7.21 (m, 2H), 7.31–7.05 (m, 2H), 5.84–5.70 (m, 1H), 4.99–4.78 (m, 3H), 4.6–4.57 (m, 2H), 4.39–4.33 (m, 1H), 2.88–2.69 (m, 2H), 2.52–2.45 (m, 2H), 2.24–2.15 (m, 1H), 1.07–1.02 (m, 6H).

EXAMPLE 27

(3S)-3-[(1-(4'-Butenyl)indole-2-Carbonyl)Valinyl] Amino-4-Oxobutanoic Acid (3S)-3-[(1-(4'-Butenyl)indole-2-carbonyl) valinyl]amino-4-oxobutanoic acid, semicarbazone (79 mg, 0.17 mmol) was dissolved in methanol (3 mL), formaldehyde (1 mL, 37% wt. aq) and acetic acid (1 mL) and the resulting mixture was stirred for 7 hours under a nitrogen atmosphere at room temperature. The reaction mixture was concentrated in vacuo, diluted with water, and extracted twice with ethyl acetate. The ethyl combined acetate solutions were washed with brine, dried over sodium sulfate and concentrated to give a crude product which was triturated with ether to afford the title product as a light purple powder (24 mg, 34%). TLC (methylene chloride:methanol:acetic acid, 20:1:1, silica gel): $R_f$=0.60; MS for $C_{22}H_{27}N_3O_5$:$M+H^+$= 414; $M-H^+$=412. $^1$H-NMR (CD$_3$OD): δ8.09–8.05 (m, 1H), 7.62 (d, J=8.0, 1H), 7.46 (dd, J=8.5, 0.8, 1H), 7.31–7.25 (m, 1H), 7.13–7.07 (m, 2H), 5.85–5.71 (m, 1H), 4.99–4.90 (m, 3H), 4.62–4.54 (m, 3H), 4.41–4.30 (m, 2H), 2.75–2.46 (m, 4H), 2.22–2.14 (m, 1H), 1.06–1.02 (m, 6H).

EXAMPLE 28

(3S)-3-[(1-(2'-(1'-t-Butoxy-1'-Oxo)Ethyl)Indole-2-Carbonyl)Alaninyl]Amino-4-Oxobutanoic Acid, t-Butyl Ester Semicarbazone 1-[2'-(1'-t-Butoxy-1'-oxo)ethyl]indole-2-carboxylic acid (220 mg, 0.8 mmol) and 3(S)-(alaninyl)amino-4-oxobutanoic acid, t-butyl ester semicarbazone (241 mg, 0.8 mmol) were dissolved in methylene chloride (3 mL) and DMF (1 mL) and the resulting solution was treated with both DMAP (89 mg, 0.8 mmol) and EDAC (211 mg. 1.1 mmol). The resultant reaction mixture was stirred for 1 hour at OEC and then an additional 3 hours at room temperature to give a white precipitate. The reaction mixture was concentrated to remove methylene chloride and quenched with 5% KHSO$_4$ solution. The white solid was collected by filtration, washed with water and ether and dried in vacuo to afford the title product as a white powder (297 mg, 66%). TLC (methanol/methylene chloride: 1/9, silica gel): $R_f$=0.27. $^1$H-NMR: (CD$_3$OD): δ7.65 (d, J=8.0, 1H), 7.41 (d, J=8.0, 1H), 7.26 (s, 1H), 7.22 (d, J=3.0, 1H), 7.16–7.11 (m, 1H), 5.32 (d, J=2.2, 2H), 4.94–4.89 (m, 1H), 4.54 (q, J=7.1, 1H), 2.76 (d, 2H), 1.48 (d, J=7.4, 3H).

EXAMPLE 29

(3S)-3-[(1-(Carboxymethyl)-Indole-2-Carbonyl) Alaninyl]Amino-4-Oxabutanoic Acid, Semicarbazone (3S)-3-[(1-(2'-(1'-t-butoxy-1'-oxo)ethyl)indole-2-carbonyl)]amino-4-oxobutanoic acid, t-butyl ester, semicarbazone (274 mg, 0.51 mmol) in methylene chloride (2 mL) was treated with TFA (1 mL). The resulting solution was stirred for 2 hours under a nitrogen atmosphere at room temperature. The reaction mixture was concentrated and chased with methylene chloride to give a solid. Trituration of the solid with ether gave the title product as a light gray powder (262 mg). TLC (methylene chloride:methanol:acetic acid, 8:1:1, silica gel): $R_f$=0.08. $^1$H-NMR (CD$_3$OD): δ7.65 (d, J=8.0, 1H), 7.41 (d, J=8.0, 1H), 7.26 (s, 1H), 7.22 (d, J=3.0, 1H), 7.16–7.11 (m, 1H), 5.32 (d, J=2.2, 2H), 4.94–4.89 (m, 1H), 4.54 (q, J=7.1, 1H), 2.76 (d, 2H), 1.48 (d, J=7.4, 3H).

EXAMPLE 30

(3S)-3-[(1-(Carboxymethyl)Indole-2-Carbonyl) Alaninyl]Amino-4-Oxobutanoic Acid (3S)-3-[(1-(Carboxymethyl)indole-2-carbonyl)alaninyl] amino-4-oxobutanoic acid, semicarbazone (241 mg, 0.47 mmol) was dissolved in methanol (3 mL), formaldehyde (1 mL, 37% wt. aq) and acetic acid (1 mL) and the resulting solution was stirred for 3 hours under a nitrogen atmosphere at room temperature. The reaction mixture was concentrated in vacuo, diluted with water and extracted twice with ethyl acetate. The combined ethyl acetate solutions were washed with brine, dried under sodium sulfate and concentrated to give a glassy material which was triturated with ether to afford the title product as a slightly yellow powder (114 mg, 63%). TLC methylene chloride:methanol:acetic acid, 8:1:1, silica gel): $R_f$=0.16. $^1$H-NMR (CD$_3$OD): $\delta$7.65 (d, J=8.0, 1H), 7.40 (d, J=8.2, 1H), 7.33–7.27 (m, 1H), 7.24 (s, 1H), 7.16–7.10 (m, 1H), 5.36 and 5.26 (AB, J=17.9, 2H), 4.64–4.50 (m, 2H), 4.34–4.20 (m, 1H), 2.72–2.48 (m, 2H), 1.45 (d, J=7.14, 3H, 2 sets).

EXAMPLE 31

(3S)-3-[(1-(3'-(1'-t-Butoxy-1'-Oxo)Propyl)Indole-2-Carbonyl)Alaninyl]Amino-4-Oxobutanoic Acid, t-Butyl Ester Semicarbazone 1-(3'-(1'-t-Butoxy-1'-oxo)propyl)indole-2-carboxylic acid (147 mg, 0.51 mmol) was dissolved in DMF 3 mL) and to the resulting solution was added both DMAP (68 mg, 0.56 mmol) and EDAC (140 mg, 0.73 mmol). Stirring was continued for 10 minutes under a nitrogen atmosphere at 0° C. (3S)-3-(Alaninyl)amino-4-oxobutanoic acid, t-butyl ester semicarbazone (154 mg, 0.51 mmol) was added to the reaction mixture, and the mixture was stirred for 1 hour at 0° C. and then an additional 4 hours at room temperature. The reaction mixture was partitioned between 5% KHSO$_4$ solution and ethyl acetate. The ethyl acetate solution was washed successively with 5% KHSO$_4$ solution, saturated sodium bicarbonate solution (2×) and brine, dried over sodium sulfate, and concentrated to give a foam as crude product. Trituration of the foam with ether afforded the title product as a white powder (161 mg 55%). TLC (methanol/methylene chloride: 1/9, silica gel): $R_f$=0.36; $^1$H-NMR (CD$_3$OD): $\delta$7.62 (d, J=8.0, 1H), 7.50 (d, J=8.2, 1H), 7.29 (t, J-8.2, 1H), 7.22 (d, J=3.0, 1H), 7.16 (s, 1H), 7.11 (t, J=7.4, 1H), 4.96–4.90 (m, 1H), 4.82–4.72 (m, 2H), 4.56 (q, J=7.1, 1H), 2.78–2.66 (m, 4H), 1.49 (d, J=7.4, 3H), 1.40 (s, 9H), 1.28 (s, 9H).

EXAMPLE 32

(3S)-3-[(1-(2'-Carboxyethyl)Indole-2-Carbonyl)Alaninyl]Amino-4-Oxobutanoic Acid, Semicarbazone (3S)-3-[(1-(3'-(1'-t-Butoxy-1'-oxo)propyl) indole-2-carbonyl)alaninyl]amino-4-oxobutanoic acid, t-butyl ester semicarbazone (140 mg, 0.24 mmol) was dissolved in anisole (0.2 mL) and methylene chloride (2 mL) and the suspension was treated with TFA (1 mL). The resulting solution was stirred for 2 hours under a nitrogen atmosphere at room temperature. The reaction mixture was concentrated and chased with methylene chloride to give a solid. Trituration of the solid with ether gave the title product as a colorless powder (107 mg, 95%). TLC (methylene chloride:methanol:acetic acid, 8:1:1, silica gel): $R_f$=0.17; $^1$H-NMR (CD$_3$OD): $\delta$7.62 (d, J=8.0, 1H), 7.50 (d, J=8.2, 1H) 7.32–7.27 (m 1H), 7.23 (d, J=3.0, 1H), 7.13–7.08 (m, 2H), 4.97–4.90 (m, 1H), 4.80–4.69 (m, 1H), 4.54 (q, J=7.1, 1H), 2.82–2.73 (m, 4H), 1.49 (d, J=7.1, 3H).

EXAMPLE 33

(3S)-3-(1-(2'-Carboxyethyl)Indole-2-Carbonyl)Alaninyl]Amino-4-Oxobutanoic Acid (3S)-3-[(1-(2'-Carboxyethyl)indole-2-carbonyl) alaninyl]amino-4-oxobutanoic acid, semicarbazone (95 mg, 0.21 mmol) was dissolved in methanol (3 mL), formaldehyde (1 mL, 37% wt. aq) and acetic acid (1 mL) and the resultant solution was stirred for 4 hours under a nitrogen atmosphere at room temperature. The reaction mixture was concentrated to remove methanol, diluted with water and extracted twice with ethyl acetate. The combined ethyl acetate solutions were washed with brine, dried over sodium sulfate and concentrated to give a glassy material which was triturated with ether to afford the title product as a slightly yellow powder (20 mg, 20%). TLC (methylene chloride:methanol:acetic acid, 8:1:1, silica gel): $R_f$=0.26; $^1$H-NMR (CD$_3$OD): $\delta$7.62 (d, J=8.0, 1H), 7.51 (d, J=1H), 7.32–7.27 (m, 1H), 7.13–7.08 (m, 2H), 4.80–4.76 (m, 2H), 4.68–4.52 (m, 2H), 4.37–4.25 (m, 1H), 2.84–2.50 (m, 3H), 1.47 (d, J=7.1, 3H, 2 sets).

EXAMPLE 34

2,6-Dichlorobenzyloxyethanol

Sodium hydride (1.76 g, 0.044 mol, 60% wt. in mineral oil) was slowly added to a solution of ethylene glycol (11.2 mL) in dry THF (100 mL). The resultant mixture was stirred briefly under a nitrogen atmosphere at room temperature. α-Bromo-2,6-dichlorotoluene (9.894 g, 0.04 mol) was added to the mixture and the mixture was stirred for an additional 5.5 hours under a nitrogen atmosphere at room temperature. Additional sodium hydride (0.400 g) was added and the mixture was then stirred for 24 hours at room temperature. The reaction mixture was concentrated to remove THF, and the residue was partitioned between ether and water. The aqueous layer was back extracted with ether (2×). The combined organic solution was washed with water and brine, dried over sodium sulfate, filtered and concentrated to give a crude oil. The oil was flash chromatographed on silica gel with ethyl acetate/hexanes (10–50%) to give the title product as a yellow oil (4.56 g, 51%). TLC (ethyl acetate/hexanes, 30/70): $R_f$=0.26. $^1$H-NMR (CDCl$_3$): $\delta$7.35–7.18 (m, 3H), 4.84 (s, 2H), 3.76–3.66 (m, 4H).

EXAMPLE 35

5-(2',6'-Dichlorobenzyloxy)-4-Hydroxy-3-Nitro-Pentanoic Acid, t-Butyl Ester

DMSO was added dropwise to a solution of (47.5 mL) oxalyl chloride (7.5 mL, 15.0 mmol, 2.0 M in methylene chloride) and the resultant reaction mixture was stirred for 10 min at −78° C. 2,6-Dichlorobenzyloxy-ethanol (2211 mg, 10 mmol) in dry methylene chloride (5 mL) was added dropwise to the mixture and the mixture was then stirred for 15 minutes under a nitrogen atmosphere at −78° C. Triethylamine (8.4 mL, 60 mmol) was added dropwise to the reaction mixture, and the resultant mixture was stirred for 10 min at −78° C. then allowed to warm to 0° C. (over a period of approximately 20 min). A methylene chloride solution of tert-butyl 3-nitropropionate (1927 mg, 11.0 mmol in 5 mL of dry methylene chloride) was added dropwise to the reaction mixture and the mixture was stirred for 1 hour. The residue was extracted with ether and the resultant white solid was collected by filtration. The organic filtrate was washed with 5% KHSO$_4$ solution (2×) and brine, dried over sodium sulfate, and concentrated to give a crude oil (3.95 g). The oil was subjected to flash chromatography on silica gel with ethyl acetate/hexanes (1:2) to afford the title product as a yellow oil (2.917 g, 74%). TLC (ethyl acetate, hexanes, 60/40): $R_f$=0.54.

EXAMPLE 36

3-Amino-5-(2',6'-Dichlorobonzyloxy)-4-Hydroxy-Pentanoic Acid, t-Butyl Ester

A mixture of 5-(2',6'-dichlorobenzyloxy)-4-hydroxy-3-nitropentanoic acid t-butyl ester (2.213 g, 0.0056 mol) and wet Raney nickel (3.4 g) in methanol (150 mL) was stirred for 2 hours under a hydrogen balloon at room temperature. The reaction mixture was filtered through Celite and the filter cake was washed with methanol. The filtrate was concentrated and chased with methylene chloride to give the title product (2.078 g, 100%). TLC (methanol/methylene chloride 1/9): $R_f$=0.21.

EXAMPLE 37

N-(1,3-Dimethylindole-2-Carbonyl)Valine

DMAP (367 mg, 3.0 mmol) and EDAC (748 mg, 3.9 mmol) were added as solids to a solution of 1,3-dimethylindole-2-carboxylic acid (568 mg, 3.3 mmol) in DMF (5 mL), the resultant mixture was stirred for 10 minutes under a nitrogen atmosphere at 0° C. A methylene chloride solution of the methyl ester of valine (553 mg, 3.3 mmol, in 5 mL of methylene chloride) was added to the mixture, and the mixture was first stirred for one hour at 0° C. then for 5 hours at room temperature. The reaction mixture was partitioned between ethyl acetate and 5% $KHSO_4$ solution and the aqueous solution was back-extracted with ethyl acetate. The combined ethyl acetate washes were in turn washed with 5% $KHSO_4$ solution saturated sodium bicarbonate solution (2×) and brine, dried over sodium sulfate, and concentrated to give the title product as a yellow syrup (900 mg).

A 1,4-dioxane solution (5 mL) of the above yellow syrup was treated with an aqueous solution of lithium hydroxide (1.0 M LiOH, 3.0 mL) and the resultant mixture was stirred for 1 hour at room temperature (the mixture became homogeneous). The reaction mixture was acidified with 1 M hydrochloric acid and extracted with ethyl acetate (3×). the combined ethyl acetate solutions were washed with brine, dried over sodium sulfate, and concentrated to give the title product as a yellow foam (839 mg).

$^1$H-NMR (CD$_3$OD): δ7.58 (dt, J=8.0, 0.8, 1H), 7.37 (dd, J–8.0, 0.8, 1H), 7.29–7.24 (m, 1H), 7.12–7.06 (m, 1H), 4.57 (d, J=5.8, 1H), 3.80 (s, 3H), 2.48 (s, 3H), 3.34–2.28(m, 1H), 1.10 (d, J=6.9, 3H), 1.07 (d, J=6.9, 3H).

EXAMPLE 38

N-[(1,3-Dimethylindole-2-Carbonyl)Valinyl]-3-Amino-4-Hydroxy-5-(2',6'-Dichlorobenzyloxy) Pentanoic Acid, t-Butyl Ester 1-Hydroxybenzotriazole hydrate (153 mg, 1.0 mmol) and EDAC (268 mg, 1.4 mmol were added to a methylene chloride solution of N-(1,3-dimethylindole-2-carbonyl) valine (288 mg, 1.0 mmol, in 3 mL of methylene chloride). The resultant mixture was stirred for 10 minutes under a nitrogen atmosphere at room temperature. A methylene chloride solution of 3-amino-5-(2',6'-dichlorobenzyloxy)-4-hydroxypentanoic acid, t-butyl ester (364 mg, 1.0 mmol, in 2 mL of methylene chloride) was added to the reaction mixture and the mixture was first stirred for one hour under a nitrogen atmosphere at 0° C., and then for 16 hours at room temperature. The reaction mixture was partitioned between ethyl acetate and 5% $KHSO_4$ solution and the aqueous solution was back-extracted with ethyl acetate. The combined ethyl acetate solutions were washed with 5% $KHSO_4$ solution, saturated sodium bicarbonate solution (2×) and brine dried over sodium sulfate, and concentrated to give crude product (583 mg). The crude product was subjected to flash chromatography on silica gel with ethyl acetate/hexane (2/3) to give the title product as a white solid (260 mg). TLC (ethyl acetate/hexanes 1:1): $R_f$=0.38.

EXAMPLE 39

N-[(1,3-Dimethylindole-2-Carbonyl)Valinyl-3-Amino-4-Oxo-5-(2',6'-Dichlorobenzyloxy)Pentanoic Acid, t-Butyl Ester Dess-Martin periodinane (195 mg) was added as a solid to a solution of N-[(1,3-dimethylindole-2-carbonyl)valinyl]-3-amino-4-hydroxy-5-(2',6'-dichlorobenzyloxy)pentanoic acid, t-butyl ester (96 mg) in DMSO (1.5 ml). The resulting solution was stirred under a nitrogen atmosphere at room temperature for thirty minutes, then partitioned between EtOAc and water. The organic phase was washed with water (2×) and brine, dried (Na$_2$SO$_4$), and concentrated to give a white solid (83 mg). Flash chromatographic purification with EtOAc/hexanes (1:1) afforded the title product as a white solid (54 mg). TLC (EtOAc/hexanes; 1:1, silica gel): $R_f$=0.52.

EXAMPLE 40

N-[1,3-Dimethylindole-2-Carbonyl)Valinyl]-3-Amino-4-Oxo-5-(2',6'-Dichlorobenzyloxy)Pentanoic Acid A solution of N-[(1,3-Dimethylindole-2-carbonyl) valinyl]-3-amino-4-oxo-5-(2',6'-dichloro-benzyloxy) pentanoic acid, t-butyl ester (49 mg) in anisole (0.2 mL) and methylene chloride (2 mL) was treated with TFA (1 mL) and stirred for 30 minutes under nitrogen atmosphere at room temperature. The resultant solution was concentrated and chased with methylene chloride to give a white solid as the crude product. The crude product was triturated with ether to yield the title product as a white powder (34 mg) MS for C$_{28}$H$_{31}$Cl$_2$N$_3$O$_6$; MH$^+$=576/578; (MH)$^-$=574/576.

EXAMPLE 41

N [(1,3-Dimethylindole-2-Carbonyl)Valinyl]-3-Amino-4-Hydroxy-5-Fluoropentanoic Acid, t-Butyl Ester 4-Dimethylaminopyridine (DMAP) (67 mg, 0.55 mmol) and 1-(3'-dimethylaminopropyl)-3-ethylcarbodiimide hydrochloride (EDAC) (125 mg, 0.65 mmol) were added as solids to a DMF solution of 1,3-dimethylindole-2-carboxylic acid (95 mg, 0.5 mmol in 1 mL of DMF), and the resultant reaction mixture was stirred for 10 minutes under a nitrogen atmosphere at 0° C. A methylene chloride solution of N-(valinyl)-3-amino-4-hydroxy-5-fluoropentanoic acid, t-butyl ester (153 mg, 0.5 mmol in 1 mL of methylene chloride) was added and the resultant reaction mixture was first stirred for 1 hour at 0° C. and then for 4 hours at room temperature. The reaction mixture was partitioned between ethyl acetate and 5% $KHSO_4$ solution and the aqueous solution was back-extracted with ethyl acetate. The combined ethyl acetate solutions were washed with 5% $KHSO_4$ solution, saturated sodium bicarbonate solution (2×), and brine, dried over sodium sulfate, and concentrated to give a solid. The solid was triturated with ether/hexane to yield the title product as a white solid (134 mg, 56%). TLC (ethyl acetate/hexanes, 2:1): $R_f$=0.42 $^1$H-NMR (CDCl$_3$): δ7.59 (d, J=8.8, 1 H), 7.37 (d, J=7.7, 1 H) , 7.29–7.24 (m, 1 H), 7.12–7.07 (m, 1 H), 4.49–4.26 (m, 5 H), 3.81–3.79 (m, 3 H), 2.66–2.47 (m, 5 H), 2.22–2.10 (m, 1 H), 1.45–1.41 (m, 9 H), 1.09–1.03 (m, 6 H).

EXAMPLE 42

N-[(1,3-Dimethylindole-2-Carbonyl)Valinyl]-3-Amino-4-Oxo-5-Fluoropentanoic Acid, t-Butyl Ester Dimethyl sulfoxide (0.09 mL, 1.25 mmol) was added to a solution of oxalyl chloride (0.19 mL, 2.0 M, 0.38 mmol)

in methylene chloride (4 mL), and the resultant mixture was stirred for 10 minutes under a nitrogen atmosphere at −78° C. A dry methylene chloride solution of N-[1,3-dimethylindole-2-carbonyl)valinyl]-3-amino-4-hydroxy-5-fluoropentanoic acid, t-butyl ester (119 mg, 0.25 mmol in 1 mL of dry methylene chloride), was added dropwise to the mixture and the resultant reaction mixture was stirred for 15 min at −78° C. Triethylamine (0.21 mL, 1.5 mmol) was added dropwise, and the reaction mixture was then stirred for 10 minutes at −78° C. then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% KHSO$_4$ solution and brine, dried over sodium sulfate, and concentrated to give a crude product. The crude product was chromatographed with ethyl acetate/hexanes (2:1) on silica gel gave the title product as a white solid (48 mg, 41%). TLC (ethyl acetate/hexanes, 2:1): R$_f$=0.58.

EXAMPLE 43

N-[(1,3-Dimethylindole-2-Carbonyl)Valinyl]-3-Amino-4-Oxo-5-Fluoropentanoic Acid

A solution of N-[(1,3-dimethylindole-2-carbonyl) valinyl]-3-amino-4-oxo-5-fluoropentanoic acid, t-butyl ester (40 mg) in anisole (0.2 mL) and methylene chloride (2 mL) was treated with trifluoroacetic acid (1 mL), and the resultant reaction mixture was stirred for 30 minutes under a nitrogen atmosphere at room temperature. The reaction mixture was concentrated and chased with methylene chloride to give a solid. The solid was triturated with ether to yield the title product as a brown powder (17 mg). TLC (methylene chloride/methanol/acetic acid, 20:1:1): R$_f$=0.40. MS for C$_{21}$H$_{26}$FN$_3$O$_5$: MH$^+$=420; MH$^+$=418.

EXAMPLE 44

N-[(1-Methylindole-2-Carbonyl)Valinyl]-3-Amino-4-Hydroxy-5-Fluoropentanoic Acid, t-Butyl Ester.

DMAP (95 mg, 0.78 mmol) and EDAC (200 mg, 1.04 mmol) were added as solid t a solution of 1-methylindole-2-carboxylic acid (130 mg, 0.74 mmol) and N-(valinyl)-3-amino-4-hydroxy-5-fluoropentanoic acid, t-butyl ester (227 mg, 0.74 mmol) in methylene chloride (5 mL), and the resultant solution was stirred for 1 hour under a nitrogen atmosphere at 0° C. and then 4 hours at room temperature. The reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated sodium bicarbonate solution (2x) and brine, dried over sodium sulfate, and concentrated to give a foam. The foam was triturated with ether to yield the title product as a slightly brown solid (224 mg, 65%). TLC (methanol/methylene chloride, 1:9): R$_f$=0.46.

EXAMPLE 45

N-[3-Chloro-1-Methylindole-2-Carbonyl)Valinyl]-3-Amino-4-Oxo-5-Fluoropentanoic Acid, t-Butyl Ester DMSO (0.06 mL, 0.9 mmol) was added to a solution of oxalyl chloride (0.14 mL, 2.0 M, 0.28 mmol, in 4 mL of methylene chloride) and the solution was then stirred for 10 minutes under a nitrogen atmosphere at −78° C. A solution of N-[(1-methylindole-2-carbonyl)valinyl]-3-amino-4-hydroxy-5-fluoropentanoic acid, t-butyl ester (85 mg, 0.18 mmol) in dry methylene chloride (1 mL), was added dropwise to the reaction mixture and the mixture was stirred for 15 minutes at −78° C. Triethylamine (0.15 mL, 1.08 mmol) was added dropwise to the reaction mixture and the mixture was stirred for 10 minutes at −78° C. and then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% KHSO$_4$ solution and brine, dried over sodium sulfate, and concentrated to give a brown foam. The foam was triturated with ether to afford the title product as a light brown powder (64 mg). MS for C$_{24}$H$_{31}$ClFN$_3$O$_5$: (MH)$^-$=494/496.

EXAMPLE 46

N-[(3-Chloro-1-Methylindole-2-Carbonyl)Valinyl-3-Amino-4-Oxo-5-Fluoropentanoic Acid A solution N-[(3-chloro-1-methylindole-2-carbonyl) valinyl]-3-amino-4-oxo-5-fluoropentanoic acid, t-butyl ester (47 mg) in anisole (0.2 mL) and methylene chloride (2 mL) as treated with TFA (1 mL) and the resultant reaction mixture was stirred for 1 hour under a nitrogen atmosphere at room temperature. The reaction mixture was concentrated and chased with methylene chloride, then triturated with ether to afford a brown powder (28 mg). The powder was subjected to flash chromatography on silica gel with methanol/methylene chloride containing a drop of acetic acid to give the title product (25 mg). TLC (methylene chloride/methanol, 9:1): R$_f$=0.29. MS for C$_{20}$H$_{23}$ClFN$_3$O$_5$: MH$^+$=440/442; (M−H)$^-$=438/440.

EXAMPLE 47

N-[(5-Fluoro-1-Methylindole-2-Carbonyl)Valinyl]-3-Amino-4-Hydroxy-5-Fluoropentanoic Acid, t-Butyl Ester DMAP (257 mg, 2.08 mmol) and EDAC (427 mg, 2.23 mmol) were added as solids to a solution of 5-fluoro-1-methylindole-2-carboxylic acid (359 mg, 86 mmol in 3 mL DMF), and the resultant reaction mixture was stirred for 10 minutes under a nitrogen atmosphere 0° C. N-(Valinyl)-3-amino-4-hydroxy-5-fluoropentanoic acid, t-butyl ester (579 mg, 1.86 mmol) in DMF (3 mL) was added and the resulting solution was stirred for 1 hour under a nitrogen atmosphere at 0° C. and 4 hours at room temperature. The reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated sodium bicarbonate solution (2x) and brine, dried over sodium sulfate; and concentrated to give the title product as a slightly yellow solid (0.827 mg). TLC (methanol/methylene chloride, 1.9): R$_f$=0.52.

EXAMPLE 48

N-[(3-Chloro-5-Fluoro-1-Methylindole-2-Carbonyl) Valinyl-3-Amino-4-Oxo-5-Fluoropentanoic Acid, t-Butyl Ester DMSO (0.60 mL, 8.5 mmol) was added to a methylene chloride solution of oxalyl chloride(2.1 mL, 2.0 M, 4.2 mmol, in 15 mL of methylene chloride), and the resultant reaction( mixture was stirred for 10 minutes under a nitrogen atmosphere at −78° C. A methylene chloride solution of N-[(5-fluoro-1-methylindole-2-carbonyl)valinyl]-3-amino-4-hydroxy-5-fluoropentanoic acid, t-butyl ester (820 mg, 1.7 mmol, in 8 mL of dry methylene chloride), and DMSO (0.4 mL) were added dropwise to the reaction mixture and stirred for 15 minutes at −78° C. TEA (1.4 mL, 10.2 mmol) was added to the mixture dropwise and the mixture was stirred for 10 minutes at −78° C., then was allowed to warm to room temperature. The reaction mixture was partitioned between ethyl acetate and 5% $KHSO_4$ solution and the aqueous layer was back-extracted with ethyl acetate. The combined ethyl acetate solutions were washed with 5% $KHSO_4$ solution and brine, dried over sodium sulfate, and concentrated to give the title product as a slightly yellow solid. Trituration with either afforded the title product as a white powder (705 mg, 85%). TLC (methanol/methylene chloride, 1:9): $R_f$=0.63. MS for $C_{24}H_{30}ClF_2N_3O_5$: $MH^+$=514/516; $(M-H)^-$=512/514.

EXAMPLE 49

N-[(1,3-Chloro-5-Fluoro-1-Methylindole-2-Carbonyl)Valinyl]-3-Amino-4-Oxo-5-Fluoropentanoic Acid A solution of N-[(3-chloro-5-fluoro-1-methylindole-2-carbonyl)valinyl]-3-amino-4-oxo-5-fluoropentanoic acid, t-butyl ester (682 mg) in anisole (1 mL) and methylene chloride (10 mL) was treated with TFA (5 mL), and the resultant reaction mixture was stirred for 45 minutes under a nitrogen atmosphere at room temperature. The reaction mixture was concentrated and chased with methylene chloride, then triturated with ether to afford the title product as a white powder (500 mg). MS for $C_{20}H_{22}ClF_2N_3O_5$: $MH^+$=458/460; $(M-H)^-$=456/458.

EXAMPLE 50

N-[(1-(3'-Phenylpropyl)Indole-2-Carbonyl)Valinyl]-3-Amino-4-Hydroxy-5-Fluoropentanoic Acid, t-Butyl Ester DMAP (122 mg, 1.0 mmol) and EDAC (249 mg 1.3 mmol) were added as solids to a DMF solution of 1-(3'-phenylpropyl)indole-2-carboxylic acid (279 mg, 1.0 mmol, 2 mL in DMF), and the resultant mixture was stirred for 10 minutes under a nitrogen atmosphere at 0° C. A methylene chloride solution of N-(valinyl)-3-amino-4-hydroxy-5-fluoropentanoic acid, t-butyl ester (306 mg, 1.0 mmol in 2 mL of methylene chloride) was added to the reaction mixture and the mixture was stirred for 1 hour under a nitrogen a mosphere at 0° C. and then 4 hours at room temperature. The yellow reaction mixture was partitioned between ethyl acetate and 5% $KHSO_4$ solution and the aqueous solution was back-extracted with ethyl acetate. The combined ethyl acetate solutions were washed with 5% $KHSO_4$ solution, saturated sodium bicarbonate solution (2×) and brine, dried over sodium sulfate, and concentrated to give a crude solid (0.827 g). The crude solid was subjected to flash chromatography on silica gel eluting with ethyl acetate/hexanes (1:2) afforded the title product as a slightly yellow solid (171 mg). TLC (ethyl acetate/hexanes 2:1): $R_f$=0.57.

EXAMPLE 51

N-(1-(3'-Phenylpropyl)indole-2-Carbonyl)Valinyl]-3-Amino-4-Oxo-5-Fluoropentanoic Acid, t-Butyl Ester DMSO (0.11 mL, 1.5 mmol) was added to a methylene chloride solution of oxalyl chloride (0.2 mL, 2.0 M, 0.44 mmol in 3.5 mL in methylene chloride), and the resultant solution was stirred for 10 minutes under a nitrogen atmosphere at −78° C. A methylene chloride solution of N-[(1-(3'-phenylpropyl)indole-2-carbonyl)valinyl]-3-amino-4-hydroxy-5-fluoropentanoic acid, t-butyl ester (169 mg, 0.3 mmol in 1.5 mL of dry methylene chloride) was added dropwise and the resulting solution stirred for 15 minutes at −78° C. Triethylamine (0.25 mL, 1.8 mmol) was added dropwise to the reaction mixture nd the mixture was stirred for 10 minutes at −78° C., then was allowed to warm to room temperature. The reaction mixture was partitioned between ethyl acetate and 5% $KHSO_4$ solution and the aqueous layer was back-extracted with ethyl acetate. The combined ethyl acetate solutions were washed with 5% $KHSO_4$ solution and brine, dried over sodium sulfate, and concentrated to give a crude product. The crude product was triturated with hexanes to yield the title product as a slightly yellow powder (129 mg, 7%). TLC (ethyl acetate/hexanes 2:1): $R_f$=0.69.

EXAMPLE 52

N-[(1-(3'-Phenylpropyl)Indole-2-Carbonyl)Valinyl]-3-Amino-4-Oxo-5-Fluoropentanoic Acid A solution of N-[(1-(3'-phenylpropyl)indole-2-carbonyl)valinyl]-3-amino-4-oxo-5-fluoropentanoic acid, t-butyl ester (97 mg) in anisole (0.2 mL) and methylene chloride (2 mL) was treated with TFA (1 mL), and the resultant reaction mixture was stirred for 1 hour under a nitrogen atmosphere at room temperature. The reaction mixture was concentrated and chased with methylene chloride, then triturated with ether to yield the title product as a slightly yellow powder (44 mg). TLC (methylene chloride/methanol/acetic acid, 20:1:1): $R_f$=0.4; MS (EI) for $C_{32}H_{40}FN_3O_5$: $MH^+$=510; $(M-H)^-$=508.

EXAMPLE 53

N-[(1-Phenylindole-2-Carbonyl)Valinyl]-3-Amino-4-Hydroxy-5-Fluoropentanoic Acid, t-Butyl Ester DMAP (122 mg, 1.0 mmol) and EDAC (249 mg, 1.3 mmol) were added as solids to a DMF solution of 1-phenylindole-2-carboxylic acid (237 mg, 1.0 mmol in 2 mL DMF), aid the resultant reaction mixture was stirred for 10 minutes under a nitrogen atmosphere at 0° C. A methylene chloride solution of N-(valinyl)-3-amino-4-hydroxy-5-fluoropentanoic acid, t-butyl ester (306 mg, 1.0 mmol in 2 mL of methylene chloride) was added to the reaction mixture and the mixture was stirred for 1 hour under a nitrogen atmosphere at 0° C. and 4 hours at room temperature. The yellow reaction mixture was positioned between ethyl acetate and 5% $KHSO_4$ solution and the aqueous solution was back-extracted with ethyl acetate. The combined ethyl acetate solutions were washed with 5% $KHSO_4$ solution, saturated sodium bicarbonate solution (2×) and brine, dried over sodium sulfate, and concentrated to give a colorless glass (0.827 g). The crude product was subjected to flash chromatography on silica gel with ethyl acetate/hexanes 1:2) to yield the title product as a white foam (400 mg, 78%). TLC (ethyl acetate/hexanes 1:1): $R_f$=0.27.

EXAMPLE 54

N-[(1-Phenylindole-2-Carbonyl)Valinyl]-3-Amino-4-Oxo-5-Fluoropentanoic Acid, t-Butyl Ester DMSO (0.13 mL, 1.9 mmol) was added to a methylene chloride solution of oxalyl chloride (0.29 mL, 2.0 M, 0.58 mmol in 4 mL of methylene chloride), and the resultant solution was stirred for 10 minutes under a nitrogen atmosphere at 78° C. A methylene chloride solution of N-[(1-phenylindole-2-carbonyl)valinyl]-3-amino-4-hydroxy-5-fluoropentanoic acid, t-butyl ester (200 mg, 0.38 mmol in 2 mL of dry methylene chloride) was added dropwise and resulting mixture stirred for 15 minutes at −78° C. Triethylamine (0.30 mL, 2.1 mmol) was added dropwise to the mixture, and the resultant mixture was stirred for 10 minutes at −78° C., then was allowed to warm to room temperature. The reaction mixture was partitioned between ethyl acetate and 5% KHSO$_4$ solution and the aqueous layer was back-extracted with ethyl acetate. The combined ethyl acetate solutions were washed with 5% KHSO$_4$ solution and brine, dried over sodium sulfate, and concentrated to give a crude product. The crude product was triturated to yield the title product as a slightly yellow powder (181 mg). TLC (ethyl acetate/hexanes 1:1): R$_f$=0.43.

EXAMPLE 55

N-[(1-Phenylindole-2-Carbonyl)Valinyl]-3-Amino-4-Oxo-5-Fluoropentanoic Acid

A solution of N-[(1-phenylindole-2-carbonyl)valinyl]-3-amino-4-oxo-5-fluoropentanoic acid, t-butyl ester (154 mg) in anisole (0.2 mL) and methylene chloride (2 mL) was treated with TFA (1 mL), and the resultant reaction mixture was stirred for one hour under nitrogen atmosphere at room temperature. The reaction mixture was concentrated and chased with methylene chloride, then triturated with ether to yield the title product as white powder (100 mg). TLC (methylene chloride/methanol/acetic acid, 20:1:1): R$_f$=0.38, MS for C$_{25}$H$_{26}$FN$_3$O$_5$: MH$^+$=468; (M−H)$^+$=466.

EXAMPLE 56

N-[1-(2'-((1'-t-Butoxy-1'-Oxo)Ethyl)indole-2-Carbonyl)Valinyl]-3-Amino-4-Hydroxy-5-Fluoropentanoic Acid, t-Butyl Ester DMAP (122 mg, 1.0 mmol) and EDAC (249 mg, 1.3 mmol) were added as solids to a DMF solution of (1-(2'-((1'-t-butoxy-1'-oxo)ethyl)indole-2-carboxylic acid (275 mg, 1.0 mmol in 2 mL of DMF), and the resultant solution was stirred for 10 minutes under a nitrogen atmosphere at 0° C. A methylene chloride solution of N-(valinyl)-3-amino-4-hydroxy-5-fluoropentanoic acid, t-butyl ester (306 mg, 1.0 mmol in 2 mL of methylene chloride) was added to it, stirred for 1 hour under a nitrogen atmosphere at 0° C. and 4 hours at room temperature. The yellow reaction mixture was partitioned between ethyl acetate and 5% KHSO$_4$ solution and the aqueous solution was back-extracted with ethyl acetate. The combined ethyl acetate solutions were washed with 5% KHSO$_4$ solution, saturated with sodium bicarbonate solution (2x) and brine, dried over sodium sulfate, and concentrated to give a colorless glass (0.827 g). The crude product was flash chromatographed on silica gel with ethyl acetate/hexane (1:1) to yield the title product as a white foam (461 mg). TLC (ethyl acetate/hexanes 30:70): R$_f$=0.11.

EXAMPLE 57

N-[(1-(2'-((1'-t-Butoxy-1'-Oxo)Ethyl)Indole-2-Carbonyl)Valinyl]-3-Amino-4-Oxo-5-Fluoropentanoic Acid, t-Butyl Ester A mixture of N-[(1-(2'-((1'-t-butoxy-1'-oxo)ethyl)indole-2-carbonyl)valinyl]-3-amino-4-hydroxy-5-fluoropentanic acid, t-butyl ester (230 mg, 0.41 mmol), N-methylmorpholine N-oxide (71 mg, 0.61 mmol) and powdered molecular sieves (205 mg) in dry methylene chloride (2 mL) was stirred for 1.5 hours under a nitrogen atmosphere at room temperature. Tetra(propyl)ammonium perruthenate (7 mg) was added and the resulting mixture was stirred for 2 hours under a nitrogen atmosphere at room temperature. The reaction mixture was filtered through silica gel with ethyl acetate as the eluent. The filtrate was concentrated and chromatographed on silica gel with ethyl acetate/hexanes (approximately 1:2 to approximately 1:1) to yield the title product as a yellow oil (100 mg). TLC (ethyl acetate/hexanes 30/70): R$_f$=0.27.

EXAMPLE 58

N-[(1-(Carboxymethyl)Indole-2-Carbonyl)Valinyl]-3-Amino-4-Oxo-5-Fluoropentanoic Acid A solution of N[(1-(2'-((1'-t-butoxy-1'-oxo)ethyl)indole-2-carbonyl)valinyl]-3-amino-4-oxo-5-fluoropentanoic acid, t-butyl ester (100 mg) in anisole (0.2 mL and methylene chloride (2 mL) was treated with TFA (1 mL). The resultant reaction mixture was stirred for 30 minutes under a nitrogen atmosphere at room temperature. The reaction mixture was concentrated and chased with methylene chloride, then triturated with ether to yield the title product as a light yellow powder (26 mg). TLC (methylene chloride/methanol, 8:1:1): R$_f$=0.32. MS for C$_{21}$H$_{24}$FN$_3$O$_7$: MH$^+$=450; (M−H)$^-$=448.

EXAMPLE 59

N-[(1-Methylindole-2-carbonyl)valinyl]-3-amino-4-hydroxy-5-fluoropentanoic Acid, t-butyl Ester To a solution of 1-methylindole-2-carboxylic acid (130 mg, 0.74 mmol) and N-(valinyl -3-amino-4-hydroxy-5-fluoropentanoic acid, tert-butyl ester in methylene chloride (5 mL) and cooled to 0° C. Solid 4-dimethylaminopyridine (DMAP) (95 mg, 0.7 mmol) and 1-(3'-dimethylaminopropyl)-3-ethylcarbodiimide hydrochloride (EDAC) (200 mg, 1.04 mmol) were added to the solution at 0° C. The reaction mixture was stirred at 0° C. for 1 h and allowed to warm slowly to room temperature. After 4 h the reaction was partitioned between ethyl acetate (EtOAc) and 5% KHSO$_4$ aqueous solution. The organic layer was washed with 5% KHSO$_4$ solution, saturated sodium bicarbonate solution, brine, dried (Na$_2$SO$_4$) and concentrated to a foam. The crude residue was triturated with diethyl ether and the solid filtered to afford the title compound as a light brown solid (224 mg, 65% yield). TLC(MeOH:CH$_2$Cl$_2$, 1:9): R$_f$=0.46.

EXAMPLE 60

N-(1-Methylindole-2-carbonyl)valinyl]-3-amino-4-oxo-5-fluoropentanoic Acid, t-butyl Ester To a solution of N-[(1-methylindole-2-carbonyl)valinyl]-3-amino-4-hydroxy-5-fluoropentanoic acid, t-butyl ester (51 mg, 0.11 mmol) in DMSO(1 mL) was added Dess-Martin periodinane (110 mg). After 30 min at room temperature the reaction mixture as partitioned between ethyl acetate and water. The organic layer was washed with water and brine, dried and concentrated to a white solid. Trituration with diethyl ether and collection of the solid afforded the title compound as a white powder (25 mg, 49% yield ). TLC (MeOH:CH$_2$Cl$_2$, 5:95): R$_f$=0.48.

EXAMPLE 61

N-[1-Methylindole-2-carbonyl)valinyl]-3-amino-4-oxo-5-fluoropentanoic Acid

A solution of N-[(1-methylindole-2-carbonyl)valinyl]-3-amino-4-oxo-5-fluoropentanoic acid, t-butyl ester (19 mg, 0.041 mmol) and anisole (0.1 mL) in $CH_2Cl_2$ (1 mL) was treated with trifluoroacetic acid (0.5 mL) at room temperature. After 30 min the reaction mixture was concentrated and chased with methylene chloride. The crude residue was triturated with diethyl ether and the solid filtered to afford the title compound as a light brown solid (12 mg, 72% yield). TLC(AcOH:MeOH:$CH_2Cl_2$, 1:1:20): $R_f$=0.59. Mass Spectrum for $C_{20}H_{24}FN_3O_5$: $[MH]^+406$, $[MH]^-404$.

Following the methods set down in Examples 59–61, the following compounds were prepared:

EXAMPLE 62

N-[(1,3-Dimethyl-5-fluoroindole-2-carbonyl) valinyl]-3-amino-4-oxo-5-fluoropentanoic acid 57% yield; TLC(MeOH:$CH_2Cl_2$, 5:95): $R_f$=0.56. Mass Spectrum for $C_{21}H_{25}F_2N_3O_5$ $[MH]^+438$, $[MH]^-436$.

EXAMPLE 63

N-[1-homoallylindole-2-carbonyl)valinyl]-3-amino-4-oxo-5-fluoropentanoic acid

29% yield; TLC(MeOH:$CH_2Cl_2$, 1:9) $R_f$=0.33. Mass Spectrum for $C_{23}H_{28}FN_3O_5$: $[MH]^+446$, $[MNa]^+468$, $[MH]^-444$.

EXAMPLE 64

N-[(1-Methyl-5-fluoroindole-2-carbonyl)valinyl]-3-amino-4-oxo-5-fluoropentanoic acid 29% yield; TLC(MeOH:$CH_2Cl_2$,9:1): $R_f$ =0.14. Mass Spectrum for $C_{20}H_{23}F_2N_3O_5$: $[MH]^+424$, $[MH]^-422$.

EXAMPLE 65

N-[(1-Methyl-3-isobutylindole--2-carbonyl)valinyl]-3-amino-4-oxo-5-fluoropentanoic acid 50% yield; TLC(MeOH:$CH_2Cl_2$,9:1): $R_f$=0.20. Mass Spectrum for $C_{24}H_{32}FN_3O_5$: $[MH]^+462$, $[MH]^-460$.

EXAMPLE 66

N-(1-Methyl-3-phenethylindolo-2-carbonyl)valinyl]-3-amino-4-oxo-5-fluoropentanoic acid 38% yield; TLC(ethyl acetate: hexanes, 1:1): $R_f$0.19. Mass Spectrum for $C_{28}H_{32}FN_3O_5$: $[MH]^+510$, $[MH]^-508$.

EXAMPLE 67

N-[(1-Methyl-5-Obenzylindole-2-carbonyl)valinyl]-3-amino-4-oxo-5-fluoropentanoic acid 78% yield; TLC(ethyl acetate: hexanes, 1:1):$R_f$=0.17. Mass Spectrum for $C_{27}H_{30}FN_3O_6$: $[MH]^+512$, $[MH]^-510$.

EXAMPLE 68

N-(1,3-Dimethyl-indole-2-carbonyl)-Valinyl-3-Amino-5-Bromo-4-Oxo-Pentanoic Acid, t-Butyl Ester 1-Hydroxybenzotriazole hydrate (3.19 g, 20.8 mmol) and 1-(3'-dimethylaminopropyl)-3-ethylcarbodiimide hydrochloride (EDAC) (5.60 g, 29.2 mmol) were added to a stirred solution of N-carbobenzyloxycarbonyl valine (5.24 g, 20.8 mmol) in methylene chloride/dimethyl formamide (DMF) (60 ml/30 ml) at $0_tC$ under nitrogen. After 15 min, aspartic acid α-methyl, β-tert-butyl diester (5.00 g, 20.8 mmol) was added as a solid followed by neat 4-methylmorpholine (2.40 ml, 21.8 mmol). After stirring at 0° C. for 1 hour and at room temperature for 5 hours, the mixture was partitioned between ethyl acetate and 5% $KHSO_4$ solution. The aqueous solution was back-extracted with ethyl acetate and the combined extracts were washed with saturated $NaHCO_3$ and brine, dried over sodium sulfate, and concentrated to give a solid. Trituration with ether afforded of N-[carbobenzylaxycarbonyl valinyl] aspartic acid, α-methyl, β-tert-butyl diester as a white solid (8.36 g, 92%). TLC($CH_2Cl_2$/MeOH, 95/5): $R_f$=0.48.

A solution of the above product (4.00 g, 9.17 mmol) in 200 mmol of methanol was stirred with palladium on activated carbon (0.45 g) under an atmosphere of hydrogen (1 atm) for 50 min. The reaction mixture was then filtered through a pad of Celite and the filter cake was washed with methanol and methylene chloride. The filtrates were combined and concentrated, and the residue was chased with methylene chloride to give N[valinyl]aspartic acid, α-methyl, β-tert-butyl diester a white solid (2.75 g, 99%). TLC ($CH_2Cl_2$/MeOH, 95/5): Rf $_f$=0.10.

To a turbid mixture of the above product (2.75 g, 9.11 mmol) and 1,3-dimethylindole-2-carboxylic acid (1.95 g, 10.3 mmol) in DMF (30 ml) was added 4-dimethylaminopyridine (DMAP) (1.26g, 10.3 mmol) and 1-(3'-dimethylaminopropyl)-3-ethylcarbodiimide hydrochloride (EDAC) (2.37 g, 12.4 mmol). The reaction mixture was stirred under a nitrogen atmosphere at $0_tC$ for 1 hour and at room temperature for 3 hours. The reaction mixture was then partitioned between ethyl acetate an 5% $KHSO_4$ solution and the aqueous solution was back-extracted with ethyl acetate. The combined extracts were washed with saturated $NaHCO_3$ solution, water, and print, dried over sodium sulfate, and concentrated to give a solid. The solid was triturated with ether to give N-[(1,3-dimethyl-indole-2-carbonyl)valinyl]aspartic acid, α-methyl, β-tert-butyl diester as a white powder (2.87 g, 67%). TLC ($CH_2Cl_2$/MeOH, 95/5): $R_f$=0.59.

An aqueous solution of lithium hydroxide (1.0 M, 2.98 ml) was added dropwise to a suspension the above product (1.41 g, 2.98 mmol) in 1,4-dioxane (10 ml). After stirring at room temperature for 30 min, the resulting clear was acidified with 1 N hydrochloric acid solution and diluted with water. The resulting white precipitate was collected by suction filtration and washed successively with water and with a small amount of ether, affording N-[(1,3-dimethyl-indole-2-carbonyl)valinyl]aspartic acid, β-tert-butyl ester as a white powder (1.18 g, 86%). TLC($CH_2Cl_2$/MeOH, 90/10): $R_f$=0.21.

To a solution of the above product (1.03 g, 2.24 mmol) and 4-methylmorphorline (0.35 ml, 3.14 mmol) in THF (20 mL) at −10° C. under nitrogen was added dropwise isobutyl chloroformate (0.380 ml, 2.92 mmol). The reaction mixture was stirred under nitrogen at $-10_tC$ for 15 min and filtered. The filter cake was washed with dry THF and the filtrates were combined and cooled to $0_tC$. The filtrates were then treated with a freshly prepared ether solution of diazomethane (excess). After the mixture was stirred at 0° C. for 1 hour, a mixture of hydrobromic acid (48% wt. aq. solution) and acetic acid (6 ml, 1/1) was added dropwise till the gas evolution ceased. After another5 min the reaction mixture was concentrated and partitioned between ethyl acetate and water. The aqueous layer was back-extracted with ethyl acetate. The organic layers ere combined, washed with water, saturated $NaHCO_3$ solution, and brine, dried over sodium sulfate, and concentrated. The residue was triturated with ether to give the title compound as a white powder (1.00 g, 83%). TLC($CH_2Cl_2$/MeOH, 95/5): $R_f$=0.88.

EXAMPLE 69

N-[(1,3-Dimethyl-indole-2-carbonyl)-Valinyl]-3-amino-5-(2,6-dichlorobenzoyl)oxy-4-oxo-pentanoic Acid, t-butyl Ester To a mixture of 2.6-dichlorobenzoic acid (0.023 g, 0.12 mmol) and potassium fluoride (0.015 g, 0.25 mmol) at room temperature under nitrogen was added N-[(1,3-dimethyl indole-2-carbonyl)valinyl]-3-amino-5-bromo-4-oxo-pentanoic acid, tert-butyl ester (0.054 g, 0.10 mmol) in one portion. After stirring at room temperature for further 16 hrs, the mixture was partitioned between ethyl acetate and water. The organic layer was washed with water, saturated NaHCO$_3$ solution, and brine, dried over sodium sulfate, and concentrated. Trituration with ether gave the title compound as a white powder (0.051 g, 79%). TLC(CH$_2$Cl$_2$/MeOH, 95/5): R$_f$=0.88.

EXAMPLE 70

N-[N-(1,3-Dimethyl-indole-2-carbonyl)-Valinyl-3-amino-5-(2,6-dichlorobenzoyl)oxy-4-oxo-pentanoic acid Trifluoroacetic acid (2 mL) was added to a stirred solution of N-(1,3-dimethyl-indole-2-carbonyl)-valinyl-3-amino-5-(2,6-dichlorobenzoyl)oxy-4-oxo-pentanoic acid, t-butyl ester (0.0340 g, 0.0526 mmol) in methylene chloride containing anisole (0.2 mL). The reaction mixture was stirred at room temperature under nitrogen for half an hour and concentrated. The residue was azeotroped with methylene chloride and triturated with ether to give the title compound as a white powder (0.0270 g, 87%). TLC(CH$_2$Cl$_2$/MeOH/AcOH, 20/1/1): R$_f$=0.43. MS for C$_{28}$H$_{29}$Cl$_2$N$_3$O$_7$, [MH]$^+$ 590/592, [MH]$^-$588/590.

Following the methods set down in Examples 69–70, the following compounds were prepared:

EXAMPLE 71

N-(1,3-Dimethyl-indole-2-carbonyl)-Valinyl-3-amino-5-(diphenylphosphinyl)oxy-4-oxo-pentanoic acid 24% yield; TLC(CH$_2$Cl$_2$/MeOH/AcOH, 20/1/1): R$_f$=0.31. MS for C$_{33}$H$_{36}$PN$_3$O$_7$, [MH]$^+$618, [MH]$^-$616.

EXAMPLE 72

N-(1,3-Dimethyl-indole-2-carbonyl)-Valinyl-3-amino-5-(1-phenyl-3-(trifluoromethyl)pyrazol-5-yl)oxy-4-oxo-pentanoic acid 49% yield; TLC(CH$_2$Cl$_2$/MeOH, 90/10): R$_f$=0.29. MS for C$_{31}$H$_{32}$F$_3$N$_5$O$_6$, [MH]$^+$628, [MH]$^-$626.

EXAMPLE 73

N-(1,3-Dimethyl-indole-2-carbonyl)-Valinyl-3-amino-5-(3-(N-phenyl)aminocarbonyl-2-naphthyl)oxy-4-oxo-pentanoic Acid 68% yield; TLC(CH$_2$Cl$_2$/MeOH, 80/20): R$_f$=0.46. MS for C$_{38}$H$_{38}$N$_4$O$_7$, [MH]$^+$663, [MH]$^-$661.

EXAMPLE 74

N-(1,3-Dimethyl-indole-2-carbonyl)-Valinyl-3-amino-5-(2-aminocarbonyl-1-phenyl)oxy-4-oxo-pentanoic Acid 61% yield; TLC(CH$_2$Cl$_2$/MeOH/HOAc, 8/1/1): R$_f$=0.32. MS for C$_{28}$H$_{32}$N$_4$O$_7$, [MH]$^+$537, [MH]$^-$535.

EXAMPLE 75

N-(1,3-Dimethyl-indole-2-carbonyl)-Valinyl-3-amino-5-(dimethylphosphinyl)oxy-4-oxo-pentanoic Acid 76% yield; TLC(CH$_2$Cl$_2$/MeOH, 90/10): R$_f$0.12. MS for C$_{23}$H$_{32}$PN$_3$O$_7$, [MH$^+$494, [MH]$^-$492.

EXAMPLE 76

N-(valinyl)aspartic acid, α-methyl, β-tert-butyl Diester

HOBt (3.19 g, 20.8 mmol) and EDAC (5.60 g, 29.2 mmol) were added to a stirred solution of N-carbobenzyloxycarbonyl valine (5.24 g, 20.8 mmol) in methylene chloride/DMF (60 ml/30 ml) at 0° C. under nitrogen. After 15 min, aspartic acid α-methyl, β-tert-butyl diester (5.00 g, 20.8 mmol) was added as a solid followed neat 4-methylmorpholine (2.40 ml, 21.8 mmol). After stirring at 0° C. for 1 hours and a room temperature for 5 hours, the mixture was partitioned between ethyl acetate and 5% KHSO$_4$ solution. The aqueous solution was back-extracted with ethyl acetate and the combined extracts were washed with saturated NaHCO$_3$ and brine, dried over sodium sulfate, and concentrated to give a solid. Trituration with ether afforded N-[carbobenzyloxycarbonylvalinyl] aspartic acid, α-methyl, β-tert-butyl diester as a white solid (8.36 g, 92%). TLC (CH$_2$Cl$_2$/MeOH, 95/5): R$_f$=0.48.

A solution of the above product (4.00 g, 9.17 mmol) in 200 mmol of methanol was stirred with palladium on activated carbon (0.45 g) under an atmosphere of hydrogen (1 atm) for 50 min. The reaction mixture was then filtered through a pad of Celite and the filter cake was washed with methanol and methylene chloride. The filtrates were combined and concentrated, and the residue was chased with methylene chloride to give the title product, N-[valinyl] aspartic acid, α-methyl, β-tert-butyl diester as a white solid (2.75 g, 99%). TLC (CH$_2$Cl$_2$/MeOH, 95/5): R$_f$=0.10.

EXAMPLE 77

N-[1,3-dimethyl-indole-2-cabonyl)valinyl]aspartic Acid, β-tert-butyl Ester

To a stirred turbid mixture of N-[valinyl]aspartic acid, α-methyl, β-tert-butyl diester 2.75 g, 9.11 mmol) and 1,3-dimethylindole-2-carboxylic acid (1.95 g, 10.3 mmol) in DMF (30 ml) was added 4-dimethylaminopyridine (DMAP) (1.26 g, 10.3 mmol) and EDAC (2.37 g, 12.4 mmol). The reaction mixture was stirred under a nitrogen atmosphere at 0° C. for 1 hour and at room temperature for 3 hours. The reaction mixture was then partitioned between ethyl acetate and 5% KHSO$_4$ solution and the aqueous solution was back-extracted with ethyl acetate. The combined extracts were washed with saturated NaHCO$_3$ solution, water, and brine, dried over sodium sulfate, and concentrated to give a solid. The solid was triturated with ether to give N-[1,3-dimethyl-indole-2-cabonyl)valinyl]aspartic acid, α-methyl, β-tert-butyl diester as a white powder (2.87 g, 67%).

An aqueous solution of LiOH (1.0 M, 2.98 mmol) was added dropwise to a suspension of the above product (1.41 g, 2.98 mmol) in 1,4-dioxane (10 ml). After stirring at room temperature for 30 min, the resulting clear solution was acidified with 1 N hydrochloric acid solution and diluted with water. The resulting white precipitate was collected by filtration and washed successively with water and with a small amount of ether, affording the title product, N-[1,3- dimethyl-indole-2-cabonyl)valinyl]aspartic acid, β-tert-butyl ester as a white solid (1.18 g, 86%). TLC (CH$_2$Cl$_2$/MeOH, 90/10): R$_f$=0.21.

EXAMPLE 78

N-[(1,3-dimethyl-indole-2-cabonyl)valinyl]-3-amino-5-bromo-4-oxo-pentanoic Acid, tert-butyl Ester To a solution of N-[1,3-dimethyl-indole-2-cabonyl) valinyl]aspartic acid, β-tert-butyl ester (1.03 g, 2.24 mmol) and 4-methylmorpholine (0.35 ml, 3.14 mmol) in THF (20 ml) at −10° C. under nitrogen was added dropwise isobutyl chloroformate (0.380 ml, 2.92 mmol). The reaction mixture was stirred under nitrogen at −10° C. for 15 min and filtered. The filter cake was washed with dry THF and the filtrates were then treated with freshly prepared ether solution of diazomethane (excess). After the mixture was stirred at 0° C. for 1 hour, a mixture of hydrobromic acid (48% wt. aq solution) ad acetic acid (6 ml, 1/1) was added dropwise till the gas evolution ceased. After another 5 min, the reaction mixture was concentrated and partitioned between ethyl acetate and water. The aqueous layer was back-extracted with ethyl acetate. The organic layers were combined, washed with saturated NaHCO$_3$ solution, and brine, dried over sodium sulfate, and concentrated. The residue was triturated with ether to give the title product, N-(1,3-dimethyl-indole-2-cabonyl)-valinyl-3-amino-5-bromo-4-oxopentanoic acid, tert-butyl ester as a white powder (1.00 g, 83%). TLC (CH$_2$Cl$_2$/MeOH, 95/5): R$_f$=0.88.

EXAMPLE 79

N-[(1,3-dimethyl-indole-2-cabonyl)valinyl]-3-amino-5-[3-(imidazol-2-yl)-naphthyl-2-oxy]-4-oxo-pentanoic Acid, tert-butyl Ester Potassium carbonate (15.5 mg, 0.112 mmol) was added to a solution of N-(1,3-dimethyl-indole-2-cabonyl)-valinyl-3-amino-5-bromo-4-oxo-pentanoic acid, tert-butyl ester (60 mg, 0.112 mmol) and 3-(imidazol-2-yl)-naphth-2-ol (23.5 mg, 0.112 mmol) in DMF (1.5 ml). After stirring at room temperature for 3 hours, the reaction mixture was partitioned between ethyl acetate and water. The aqueous layer was back-extracted extracted with ethyl acetate. The organic layers were combined, washed with saturated NaHCO$_3$ solution, and brine, dried over sodium sulfate, and concentrated. The residue was triturated with ether to give the title product, N-(1,3-dimethyl-indole-2-cabonyl)valinyl-3-amino-5-[3-(imidazol-2-yl)-naphthyl-2-oxy]-4-oxo-pentanoic acid, tert-butyl ester as a greenish solid (21.8 mg, 29%). TLC (CH$_2$Cl$_2$/MeOH, 90/10): R$_f$=0.49.

EXAMPLE 80

N-[(1,3-dimethyl-indole-2-cabonyl)valinyl]-3-amino-5-[3-(imidazol-2-yl)-naphthyl-2-oxy]-4-oxo-pentanoic Acid Trifluoroacetic acid (1.0 ml) was added to a solution of N-(1,3-dimethyl-indole-2-cabonyl)-valinyl-3-amino-5-[3-(imidazol-2-yl)-naphthyl-2-oxy]-4-oxo-pentanoic acid, tert-butyl ester (21.8 mg, 0.032 mmol) in methylene chloride (2.0 ml) containing anisole (0.30 ml). The mixture was stirred under nitrogen for 1.5 hour and concentrated. The residue was re-dissolved in methylene chloride and concentrated and triturated with ether to give the titled product as a pale brown powder (17.4 mg, 89%). TLC (CH$_2$Cl$_2$/MeOH, 90/10): R$_f$ 0.12. MS C$_{34}$H$_{35}$N$_5$O$_6$, [MH]$^+$610, [MH]$^-$=608.

EXAMPLE 81

N-[(1-methyl-3-isobutyl-indole-2-cabonyl)valinyl]-3-amino-5-bromo-4-oxo-pentanoic Acid, tert-butyl Ester The titled product was prepared in the same way as described in Examples 77 and 78, starting from 1-methyl-3-isobutyl-indole-2-carboxylic acid and the titled product of Example 76.

EXAMPLE 82

N-[(1-methyl-3-isobutyl-indole-2-cabonyl)valinyl]-3-amino-4-oxo-5-(2,3,5,6-tetrafluorophenyloxy)-pentanoic acid, tert-butyl Ester Potassium fluoride (21.6 mg, 0.37 mmol) was added to a solution of N-[(1-methyl-3-isobutyl-indole-2-cabonyl)valinyl]-3-amino-5-bromo-4-oxo-pentanoic acid, tert-butyl ester (86.1 mg, 0.149 mmol) and 2,3,5, 6-tetrafluorophenol (27.0 mg, 0.163 mmol in DMF (2.0 ml). After stirring at room temperature for 3 hours, the reaction mixture was partitioned between ethyl acetate and water. The aqueous layer was back-extracted with ethyl acetate. The organic layers were combined, washed with saturated NaHCO$_3$ solution, and brine, dried over sodium sulfate, and concentrated. The residue was triturated with ether to give the titled product, N-(1-methyl-3-isobutyl-indole-2-cabonyl)-valinyl-3-amino-4-oxo-5-(2,3,5,6-tetrafluorophenyloxy)-pentanoic acid, tert-butyl ester as a white solid (43.8 mg, 44%). TLC (hexane/EtOAc, 50/50): R$_f$=0.50.

EXAMPLE 83

N-[(1-methyl-3-isobutyl-indole-2-cabonyl)valinyl]-3-amino-4-oxo-5-(2,3,5,6-tetrafluorophenyloxy)-pentanoic Acid Treatment of N-(1-methyl-3-isobutyl-indole-2-cabonyl)-valinyl-3-amino-4-oxo-5-(2,3,5,6-tetrafluorophenyloxy)-pentanoic acid, tert-butyl ester (40 mg, 0.060 mmol) with TFA as described in Example 80 gave the titled product (23.5 mg, 0.039 mmol) as a white solid. MS C$_{30}$H$_{33}$F$_4$N$_3$O$_6$, [M+H]$^+$=608, [M−H]$^-$=606.

EXAMPLE 84

N-[(1-methyl-3-isobutyl-indole-2-cabonyl)valinyl]-3-amino-4-oxo-5-(4-fluorophenyloxy)-pentanoic Acid, tert-butyl Ester The titled product (72 mg, 100%) was prepared as a white solid as described in Example 82 using the product of Example 81 (68.0 mg, 0.12 mmol), potassium fluoride (15.6 mg, 0.27 mmol), and 4-fluorophenol (13.4 mg, 0.12 mmol) in DMF (2.0 ml) TLC (hexane/EtOAc, 50/50): R$_f$=0.48.

EXAMPLE 85

N-[(1-methyl-3-isobutyl-indole-2-cabonyl)valinyl]-3-amino-4-oxo-5-(4-fluorophenyloxy)-pentanoic Acid Treatment of the product of Example 84 (72 mg, 0.118 mmol) with TFA as described in Example 80 gave the titled product (42.0 mg, 68%) as a pale yellow powder. MS $_{30}$H$_{36}$FN$_3$O$_6$, [M+Na]$^+$=576, [M−H]$^{-=552.}$ TLC (hexane/EtOAc, 50/50): R$_f$=0.33.

EXAMPLE 86

N-(1-methyl-3-isobutyl-indole-2-cabonyl)valinyl]-3-amino-4-oxo-5-(2-fluorophenyloxy)-pentanoic Acid, tert-butyl Ester The titled product (76 mg, 100%) was prepared as a white solid as described in Example 82 using the product of Example 81 (72.0 mg, 0.124 mmol), potassium fluoride (16.5 mg, 0.284 mmol), and 2-fluorophenol (13.9 mg, 0.124 mmol) in DMF (2.0 ml). TLC (hexane/EtOAc, 50/50): $R_f$=0.44.

EXAMPLE 87

N-[(1-methyl-3-isobutyl-indole-2-cabonyl)valinyl]-3-amino-4-oxo-5-(2-fluorophenyloxy)-pentanoic Acid Treatment of N-[(1-methyl-3-isobutyl-indole-2-cabonyl) valinyl]-3-amino-4-oxo-5-(2-fluorophenyloxy)-pentanoic acid, tert-butyl ester (76 mg, 0.124 mmol) with TFA as described in Example 80 gave the titled product (25.0 mg, 36%) as a white powder. MS $C_{30}H_{36}FN_3O_6$, $[M+Na]^+$=554, $[M^-]$=552. TLC (hexane/EtOAc, 50/50) $R_f$=0.21.

EXAMPLE 88

N-[(1-methyl-3-isobutyl-indole-2-cabonyl)leucinyl]-3-amino-5-bromo-4-oxopentanoic Acid, tert-butyl Ester The titled product was prepared in the same way as described in Examples 77 and 78 using leucine instead of valine. The titled product was obtained as a white powder with $R_f$=0.39 (hexane/EtOAc, 1/1).

EXAMPLE 89

N-[(1-methyl-3-isobutyl-indole-2-cabonyl)leucinyl]-3-amino-5-(2,6-dichlorobenzoyl)oxy-4-oxo pentanoic Acid, tert-butyl Ester The titled product (63 mg, 100%, white solid) was prepared as described in Example 82 using N-[(1-methyl-3-isobutyl-indole-2-cabonyl)leucinyl]-3-amino-5-bromo-4-oxo-pentanoic acid, tert-butyl ester (52.9 mg, 0.089 mmol), potassium fluoride (13.0 mg, 0.22 mmol), and 2,6-dichlorobenzoic acid (17.1 mg, 0.089 mmol) in DMF (2.0 ml). TLC (hexane/EtOAc, 50/50): $R_f$=0.39.

EXAMPLE 90

N-[(1-methyl-3-isobutyl-indole-2-cabonyl)leucinyl]-3-amino-5-(2,6-dichlorobenzoyl)oxy-4-oxo pentanoic Acid Treatment of N-[(1-methyl-3-isobutyl-indole-2-cabonyl) leucinyl]-3-amino-5-(2,6-dichlorobenzoyl) oxy-4-oxo pentanoic acid, tert-butyl ester (63 mg, 0.089 mmol) with TFA as described in Example 80 gave the titled product (34.5 mg, 60%) as a white powder. MS $C_{32}H_{37}Cl_2N_3O_7$, $[M+H]^+$=646, $[M-H]^-$=644. TLC ($CH_2Cl_2$/MeOH, 90/10): $R_f$=0.23.

EXAMPLE 91

N-[(1-methyl-3-isobutyl-indole-2-cabonyl)leucinyl]-3-amino-4-oxo-5-(2,3,5,6-tetrafluorophenyloxy Acid, tert-butyl Ester The titled product (47.6 mg, 72%, white solid) was prepared as described in Example 82 using the product of Example 88 (57.6 mg, 0.097 mmol), potassium fluoride (18.5 mg, 0.24 mmol), and 2,3,5,6-tetrafluorophenol (21.1 mg, 0.097 mmol) in DMF (2.0 ml). TLC (hexane/EtOAc, 50/150): $R_f$=0.55.

EXAMPLE 92

N-[(1-methyl-3-isobutyl-indole-2-cabonyl)leucinyl]-3-amino-4-oxo-5-(2,3,5,6-tetrafluorophenyloxy)-pentanoic Acid Treatment of N-[(1-methyl-3-isobutyl-indole-2-cabonyl) leucinyl]-3-amino-4-oxo-5-(2,3,5,6-tetrafluorophenyloxy)-pentanoic acid, tert-butyl ester (47.6 mg, 0.070 mmol) with TFA as described in Example 80 gave the titled product (29.0 mg, 67%) as a white powder. MS $C_{35}H_{43}F_4N_3O_6$, $[M+Na]^+$=644, $[M-H]^-$=620. TLC ($CH_2Cl_2$/MeOH, 90/10): $R_f$=0.19.

EXAMPLE 93

N-[(1-methyl-3-isobutyl-indole-2-cabonyl)leucinyl]-3-amino-5-(diphenylphosphoroxy)-4-oxo-pentanoic Acid, tert-butyl Ester The titled product (30.0 mg, 93%, an oil) was prepared as described in Example 82 using the product of Example 88 (26.2 mg, 0.044 mmol), potassium fluoride (6.4 mg, 0.11 mmol), and diphenylphosphinic acid (9.7 mg, 0.044 mmol) in DMF (2.0 ml) TLC (hexane/EtOAc, 50/50): $R_f$=0.11.

EXAMPLE 94

N-[(1-methyl-3-isobutyl-indole-2-cabonyl)leucinyl]-3-amino-5-(diphenylphosphoroxy)-4-oxo-pentanoic Acid Treatment of N-[(1-methyl-3-isobutyl-indole-2-cabonyl) leucinyl]-3-amino-5-(diphenylphosphoroxy)-4-oxo-pentanoic acid, tert-butyl ester (30.0 mg, 0.041 mmol) with TFA as described in Example 80 gave the titled product (13.7 mg, 50%) as a white powder. MS $C_{37}H_{44}N_3O_7P$, $[M+Na]^+$=696, $[M-H]^-$=672. TLC ($CH_2Cl_2$/MeOH, 90/10): $R_f$=0.22.

EXAMPLE 95

N-[(1-methyl-3-isobutyl-indole-2-cabonyl) cyclohexylalaninyl]-3-amino-5-bromo-4-oxo-pentanoic Acid, tert-butyl Ester The titled product was prepared in the same way as described in Examples 77 and 78 using cyclohexylalanine instead of valine, giving the titled compound as white powder. $R_f$=0.22 (hexane/EtOAc, 3/1).

EXAMPLE 96

N-[(1-methyl-3-isobutyl-indole-2-cabonyl) cyclohexylalaninyl]-3-amino-4-oxo-5-(2,5,6-tetrafluorophenyloxy)-pentanoic Acid, tert-butyl Ester The titled product was prepared as described in Example 82 using N-[(1-methyl-3-isobutyl-indole-2-cabonyl) cyclohexylalaninyl]-3-amino-5-bromo-4-oxo-pentanoic acid tert-butyl ester (50.8 mg, 0.08 mmol), potassium fluoride (12.0 mg, 0.21 mmol), and 2,3,5,6-tetrafluorophenol (13.3 mg, 0.08 mmol) in DMF (2.0 ml). TLC (hexane/EtOAc, 3/1): $R_f$=0.25.

EXAMPLE 97

N-[(1-methyl-3-isobutyl-indole-2-cabonyl) cyclohexylalaninyl]-3-amino-4-oxo-5-(2,3,5,6-tetrafluorophenyloxy)-pentanoic Acid Treatment of N-[(1-methyl-3-isobutyl-indole-2-cabonyl) cyclohexylalaninyl]-3-amino-4-oxo-5-(2,3,5,6-tetrafluorophenyloxy)-pentanoic acid, tert-butyl ester with TFA as described in Example 80 gave the titled product (55.5 mg) as a white powder. MS $C_{34}H_{39}F_4N_3O_6$, $[M+Na]^+$=684, $[M-H]^-$=660. TLC ($CH_2Cl_2$/MeOH, 90/10): $R_f$=0.24.

EXAMPLE 98

N-[(1-methyl-3-isobutyl-indole-2-cabonyl)
cyclohexylalaninyl]-3-amino -5-(2,6-
dichlorobenzoyl)oxy--4-oxo-pentanoic Acid, tert-
butyl Ester The titled product was prepared as described in Example 82 using the product of Example 95 (72 mg, 0.114 mmol), potassium fluoride (16.5 mg, 0.28 mmol), and 2,6-dichlorobenzoic acid (21.8 mg, 0.114 mmol) in DMF (2.0 ml). TLC (hexane /EtOAc, 3/1): $R_f$=0.20.

EXAMPLE 99

N-[(1-methyl -3-isobutyl-indole-2-carbonyl)
cyclohexylalaninyl]-3-amino -5-(2,6-
dichlorobenzoyl)oxy-4-oxo-pentanoic Acid Treatment of N-[(1-methyl-3-isobutyl-indole-2-cabonyl) cyclohexylalaninyl]-3-amino -5-(2,6-dichlorobenzoyl)oxy-4-oxo-pentanoic acid, tert-butyl ester with TFA as described in Example 80 gave the titled product (54.2 mg) as a white powder. MS $C_{35}H_{41}Cl_2N_3O_7$, $[M+H]^+$=686, $[M-H]^-$=684. TLC ($CH_2Cl_2$/MeOH , 90/10): $R_f$=0.30.

EXAMPLE 100

N-[(1-methyl-3-isobutyl-indole-2-cabonyl)
cyclohexylalaninyl]-3-amino-4-oxo-5-[1-phenyl-3-
(trifluoromethyl)pyrazol-5-yloxy]-pentanoic Acid,
tert-butyl Ester The titled product (55 mg, 82%) was prepared as described in Example 82 using the product of Example 95 (54.7 mg, 0.086 mmol), potassium fluoride (12.6 mg, 0.22 mmol), and 1-phenyl-3-(trifluoromethyl)pyrazol-5-ol (19.7 mg, 0.086 mmol) in DMF (2.0 ml). TLC (hexane/EtOAc, 2/1): $R_f$=0.29.

EXAMPLE 101

N-[(1-methyl-3-isobutyl-indole-2-cabonyl)
cyclohexylalaninyl]-3-amino-3-oxo-5-[1-phenyl-3-
(trifluoromethyl)pyrazol-5-yloxy]-pentanoic Acid Treatment of N-[(1-methyl-3-isobutyl-indole-2-cabonyl) cyclohexylalaninyl]-3-amino-4-oxo-5-[1-phenyl-3-(trifluoromethyl)pyrazol-5-yloxy]-pentanoic acid, tert-butyl ester (55 mg, 0.071 mmol) with TFA as described in Example 80 gave the titled product (24.6 mg, 48%) as a white powder. MS $C_{38}H_{44}F_4N_5O_6$, $[M+H]^+$=746, $[M-H]^{31}$=722. TLC ($CH_2Cl_2$/MeOH, 90/10): $R_f$=0.26.

EXAMPLE 102

N-[(carbobenzyloxycarbonyl)-valinyl] aspartic acid,
β-tert-butyl Ester

To a dry flask under nitrogen was added H-Asp(OtBu)-OH (12.07 g, 63.8 mmol) and dry $CH_3CN$ (210 ml). The cloudy solution was stirred and treated with neat BSTFA 34 ml, 127.5 mmol) via syringe. After stirring at room temperature for 30 min., a clear solution was obtained. To this solution was added Z-Val-O-Su (22.2 g, 63.8 mmol) a a solid in one portion. The resultant solution was stirred under nitrogen at room temperature for 48 hours. The solvents were removed in vacuo and the residue treated with 300 mL of water and extracted with EtOAc (2×). The combined organic layers were washed with 5% $KHSO_4$, brine, dried over $Na_2SO_4$, filtered and concentrated to give the crude product (41.55 g, 98.34 mmol, >100%) as an oil. The resultant solid was triturated with ether to provide the titled product as a white solid (21.1 g, 78%) MS $C_{21}H_{30}N_2O_7$, $[M=Na]^+$=445, $[M-H]^-$=421.

EXAMPLE 103

N-[(carbobenzyloxycarbonyl)valinyl]-3-amino-5-
bromo4-oxo-pentanoic acid, tert-butyl Ester The procedure of Example 78 was followed, but using N-[(carbobenzyloxycarbonyl)-valinyl]aspartic acid, β-tert-butyl ester to prepare the titled product as a white solid (6.39 g, 12.80 mmol, 85%). MS $C_{22}H_{31}BrN_2O_6$, $[M+Na]^+$=521/523, $[M-H]^-$=497/499.

EXAMPLE 104

N-[(carbobenzyloxycarbonyl)valinyl]-3-amino-4-
oxo-5-(2,3,5,6-tetrafluorophenyloxy)-pentanoic
Acid, tert-butyl Ester To a solution of N-[(carbobenzyloxycarbonyl)valinyl]-3-amino-5-bromo-4-oxo-pentanoic acid, tert-butyl ester (3.36 g, 6.73 mmol) in acetone (20 ml) was added dry NaI (0.20 g, 1.35 mmol) and potassium (2,3,5,6-tetrafluoro)-phenoxide (1.37 g, 6.73 mmol) at room temperature and stirred for 1 hour. The reaction mixture was diluted with EtOAc, washed with brine, dried over $Na_2SO_4$, filtered and concentrated. The resultant solid was triturated with ether to provide the titled product as a white solid (3.53 g, 6.04 mmol, 89%). MS $C_{28}H_{32}N_2O_7$, $[M+Na]^+$=607, $[M-H]^-$= 583.

EXAMPLE 105

N-[(carbobenzyloxycarbonyl)valinyl]-3-amino-4-
hydroxy-5-(2,3,5,6-tetrafluorophenyloxy)-pentanoic
Acid, tert-butyl Ester A solution of N-[(carbobenzyloxycarbonyl)valinyl]-3-amino-4-oxo-5-(2,3,5,6-tetrafuorophenyloxy)-pentanoic Acid, tert-butyl ester (6.18 g)10.57 mmol) in 1:1 MeOH/THF (100 ml) was cooled to 0° C. and $NaBH_4$ (1.20 g, 31.72 mmol) was added and stirred for 2 hours. The reaction was diluted with saturated $NH_4Cl$ and extracted with $CH_2Cl_2$ (2×) . The combined organic layers were washed with brine, dried over $Na_2SO_4$, filtered and concentrated to give the titled product as a white solid (6.14 g, 10.46 mmol, 98%). MS $C_{28}H_{34}N_2O_7$, $[M+Na]^+$=609, $[M-H]^-$=585.

EXAMPLE 106

N-(valinyl -3-amino-4-hydroxy-5-(2,3,5,6-
tetrafluorophenyloxy)-pentanoic Acid, tert-butyl
Ester To a solution of N-[(carbobenzyloxycarbonyl)valinyl]-3-amino-4-hydroxy-5-(2,3,5,6-tetrafluorophenyloxy)-pentanoic acid, tert-butyl ester (6.12 g, 10.50 mmol) in MeOH (300 ml) was added 10% palladium on carbon (0.92 g) at room temperature. The reaction was stirred for 3 hours under hydrogen (1 atm), then filtered through a pad of celite. The filter cake was washed with MeOH. The filtrate was concentrated in vacuo to provide the titled product as a viscous yellow oil (4.69 g, 10.30 mmol, 98%) MS $C_{20}H_{20}N_2O_5$, $[M+Na]^+$=475, $[M-H]^-$=451.

EXAMPLE 107

N-[(1,3-dimethyl-indole-2-cabonyl)valinyl]-3-
amino-4-hydroxy-5-(2,3,5,6-tetrafluorophenyloxy)-
pentanoic Acid, tert-butyl Ester The procedure of Example 77 was followed using N-(valinyl)-3-amino-4-hydroxy-5-(2,3,5,6- tetrafluorophenyloxy)-pentanoic acid, tert-butyl ester (213.9 mg, 0.47 mmol), 1,3-dimethylindole-2-carboxylic acid (107 mg, 0.57 mmol), NMM (0.3 ml, 2.8 mmol), HOBt (151 mg, 0.99 mmol), and EDAC (198 mg, 1.04 mmol) in methylene chloride to prepare the titled product (210 mg, 71%).

EXAMPLE 108

N-(1,3-dimethyl-indole-2-cabonyl)valinyl]-3-amino-4-oxo-5-(2,3,5,6-tetrafluorophenyloxy)-pentanoic Acid, tert-butyl Ester To a solution of N-[(1,3-dimethyl-indole-2-cabonyl) valinyl]-3-amino-4-hydroxy-5-(2,3,5,6-tetrafluorophenyloxy)-pentanoic acid, tert-butyl ester (209 mg, 0.33 mmol) in $CH_2Cl_2$(5.0 ml) was added Dess-Martin periodinane (181 mg, 0.43 mmol) and the solution stirred for 10 min. at room temperature. The reaction was quenched with $Na_2S_2O_4$, diluted with EtOAc, washed with $NaHCO_3$, and brine, dried over $Na_2SO_4$, filtered and concentrated in vacuo. The crude product was purified by chromatography (1:1 EtOAc/hexane) to give the titled product as a white solid (135 mg, 64%).

EXAMPLE 109

N-[(1,3-dimethyl-indole-2-cabonyl)valinyl]-3-amino-4-oxo-5-(2,3,5,6-tetrafluorophenyloxy)-pentanoic Acid The procedure of Example 80 was followed using N-[(1,3-dimethyl-indole-2-cabonyl)valinyl]-3-amino-4-oxo-5-(2,3,5,6-tetrafluorophenyloxy)-pentanoic acid, tert-butyl ester to prepare the titled product. MS $C_{27}H_{27}F_4N_3O_6$, $[M+Na]^+$ 588, $[M-H]^-$=564.

EXAMPLE 110

N-[(1-methyl-indole-2-cabonyl)valinyl]-3-amino-4-hydroxy-5-(2,3,5,6-tetrafluorophenyloxy)-pentanoic Acid, tert-butyl Ester The procedure of Example 77 was followed using the product of Example 106 (197.0 mg, 0.44 mmol), 1-methylindole-2-carboxylic acid (152 mg, 0.87 mmol), NMM (0.047 ml, 0.44 mmol), HOBt (144 mg, 0.96 mmol), and EDAC (183 mg, 0.96 mmol) in methylene chloride to prepare the titled product (156 mg, 58%).

EXAMPLE 111

N-[(1-methyl-indole-2-cabonyl)valinyl]-3-amino-4-oxo-5-(2,3,5,6-tetrafluorophenyloxy)-pentanoic Acid, tert-butyl Ester To a solution of N-[(1-methyl-indole-2-cabonyl)valinyl]-3-amino-4-hydroxy-5-(2,3,5,6-tetrafluorophenyloxy)-pentanoic acid, tert-butyl ester (141 mg, 0.23 mmol) in $CH_2Cl_2$(5.0 ml) was added Dess-Martin periodinane (128 mg, 0.3 mmol) and the solution stirred for 10 min. at room temperature. The reaction was quenched with $Na_2S_2O_4$, diluted with EtOAc, washed with $NaHCO_3$, and brine, dried over $Na_2SO_4$, filtered and concentrated in vacuo. The crude product was purified by chromatography (1:1 EtOAc/hexane) to give the titled product as a white solid (129 mg, 92%).

EXAMPLE 112

N-[(1-methyl-indole-2-cabonyl)valinyl]-3-amino-4-oxo-5-(2,3,5,6-tetrafluorophenyloxy)-pentanoic Acid Treatment of N-[(1-methyl-indole-2-cabonyl)valinyl]-3-amino-4-oxo-5-(2,3,5,6-tetrafluorophenyloxy)-pentanoic acid, tert-butyl ester (120 mg, 0.20 mmol) with TFA as d scribed in Example 80 gave the titled product (104 mg, 95%) as a white powder. MS $C_{26}H_{25}F_4N_3O_6$, $[M+Na]^+$=574, $[M-H]^-$=550.

EXAMPLE 113

N-[(5-fluoro-1-methyl-indole-2-cabonyl)valinyl]-3-amino-4-hydroxy-5-(2,3,5,6-tetrafluorophenyloxy)-pentanoic Acid, tert-butyl Ester The procedure of Example 77 was followed using the product of Example 106 (212.5 mg, 0.47 mmol), 5-fluoro-1-methylindole-2-carboxylic acid (181 mg, 0.94 mmol), NMM (0.05 ml, 0.44 mmol), HOBt (151 mg, 1.03 mmol), and EDAC (196 mg, 1.03 mmol) in methylene chloride to prepare the title product.

EXAMPLE 114

N-[(5-fluoro-1-methyl-indole-2-cabonyl)valinyl]-3-amino-4-oxo-5-(2,3,5,6-tetrafluorophenyloxy)-pentanoic Acid, tert-butyl Ester To a solution of N-[(5-fluoro-1-methyl-indole-2-cabonyl) valinyl]-3-amino-4-hydroxy-5-(2,3,5,6-tetrafluorophenyloxy)-pentanoic acid, tert-butyl ester (112.6 mg, 0.8 mmol) in $CH_2Cl_2$(5.0 ml) was added Dess-Martin periodinane (95 mg, 0.22 mmol) al d the solution stirred for 10 min. at room temperature. The reaction was quenched with $Na_2S_2O_4$, diluted with EtOAc, washed with $NaHCO_3$, and brine, dried over $Na_2SO_4$, filtered and concentrated in vacuo. The crude product was purified by chromatography (1:1 EtOAc/hexane) to give the titled product as a white solid (which was directly taken to the next step in Example 115).

EXAMPLE 115

N-[(5-fluoro-1-methyl-indole-2-cabonyl)valinyl]-3-amino-4-oxo-5-(2,3,5,6-tetrafluorophenyloxy)-pentanoic Acid Treatment of the product from Example 114 with TFA as described in Example 80 gave the titled product (43 mg, 42%) as a white powder MS $C_{26}H_{24}F_5N_3O_6$, M+Na$]^+$=592, $[M-H]^-$=568.

EXAMPLE 116

N-{[1-(tert-butyl)oxycarbonylmethyl-indole-2-cabonyl]valinyl}-3-amino-4-hydroxy-5-(2,3,5,6-tetrafluorophenyloxy)-pentanoic Acid, tert-butyl Ester The procedure of Example 77 was followed using the product of Example 106 (400.0 mg, 0.90 mmol), 1-[(tert-butyloxycarbonyl)methyl]indole-2-carboxylic acid (200 mg, 0.73 mmol), NMM (0.1 ml), HOBt (246 mg, 1.63 mmol), and EDAC (304 mg, 1.60 mmol) in methylene chloride to prepare the titled product (341 mg, 68%).

EXAMPLE 117

N-{[1-(tert-butyl)oxycarbonylmethyl-indole-2-cabonyl]valinyl}-3-amino-4-oxo-5-(2,3,5,6-tetrafluorophenyloxy)-pentanoic Acid, tert-butyl Ester To a solution of N-{[1-(tert-butyl)oxycarbonylmethyl-indole-2-cabonyl]valinyl}-3-amino4-hydroxy-5-(2,3,5,6- tetrafluorophenyloxy)-pentanoic acid, tert-butyl ester (290 mg, 0.42 mmol) in CH$_2$Cl$_2$(5.0 ml) was added Dess-Martin periodinane (204 mg, 0.48 mmol) and the solution stirred for 10 min. at room temperature. The reaction was quenched with Na$_2$S$_2$O$_4$, diluted with EtOAc, washed with NaHCO$_3$, and brine, dried over Na$_2$SO$_4$, filtered and concentrated in vacuo. The crude product was purified by chromatography (1:1 EtOAc/hexane) to give the titled product as a white solid (235 mg, 82%).

EXAMPLE 118

N-{[1-(carboxymethyl)-indole-2-cabonyl]valinyl-3-amino-4-oxo-5-(2,3,5,6-tetrafluorophenyloxy)-pentanoic Acid Treatment of N-55 [1(tert-butyl)oxycarbonylmethyl-indole-2-cabonyl]valinyl }-3-amino-4-oxo-5-(2,3,5,6-tetrafluorophenyloxy)-pentanoic acid, tert-butyl ester with TFA as described in Example 80 gave the titled product as a white powder. MS C$_{27}$H$_{25}$F$_4$N$_3$O$_8$, M+H]$^+$=596, [M–H]$^-$=594.

EXAMPLE 119

Activity of Representative Compounds

IC$_{50}$ Values

The representative compounds listed in Table 1 were assayed by the forth in Example 1A.

TABLE 1

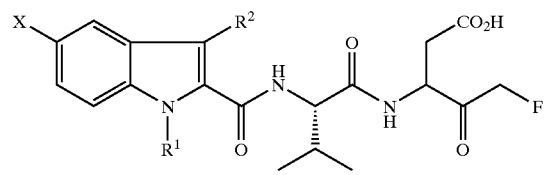

Formula A

50% INHIBITORY CONCENTRATIONS IC$_{50}$ FOR FORMULA A

| Example | R$^1$ | A | mICE IC$_{50}$ ($\mu$M) | CPP32 IC$_{50}$ ($\mu$M) |
|---|---|---|---|---|
| 4 | CH$_3$ | Ala | 0.177 | >10 |
| 7 | CH$_3$ | Pro | 11.7 | >50 |
| 10 | CH$_3$ | Val | 0.531 | 2.48 |
| 13 | CH$_3$ | Leu | 5.52 | 5.62 |
| 16 | CH$_3$ | Phe | 3.34 | 49.8 |
| 21 | CH$_3$ | Gly | 34.7 | >50 |
| 24 | CH$_2$Ph | Ala | 0.393 | >50 |
| 27 | (CH$_2$)$_2$CH=CH$_2$ | Val | 0.313 | 1.45 |
| 30 | CH$_2$CO$_2$H | Ala | 1.63 | >50 |
| 33 | (CH$_2$)$_2$CO$_2$H | Ala | 0.198 | >50 |
| reference | — | — | 0.064 | 47.0 |

B. K$_i$ Values

Representative compounds of Formula B below were assayed by the procedures set forth in Example 1B.

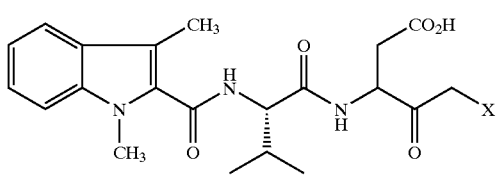

Formula B

The compounds of Examples 43, 46, 49, 52, 55, 58 and 61–67 were found to have K$_i$ values (mICE of less than 5 $\mu$M, while compounds 52, 55´, 58, 61–64 and 66–67 had K$_i$ values of less than 1 $\mu$M.

Representative compounds of Formula C below were also assayed by the procedures set forth in Example 1B.

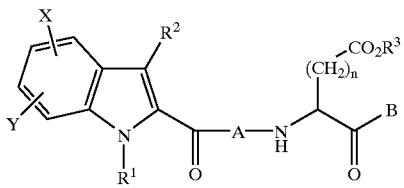

Formula C

The compounds of Examples 43 and 70–75 had K$_i$ values (mICE) of 8 $\mu$M or less, while compounds 71, 72 and 74 had K$_i$ values of less than 1 $\mu$M.

In addition, compounds of Examples 80, 83, 87, 90, 92, 94, 97, 99, 101, 109, 112, 115 and 118 were found to have an IC$_{50}$ (mICE) of less than 1 $\mu$M.

Although the invention has been described with reference to the examples provided above, it should be understood that various modifications can be made without departing from the spirit of the invention. Accordingly, the invention is limited only for the claims.

We claim:

1. A compound of the following Formula I:

Formula I wherein;

n is 1 or 2;

A is a natural amino acid;

B is halomethyl, CH$_2$OR$^6$, CH$_2$OC(=O)R$^6$ or CH$_2$OPO(R$^7$)R$^8$;

R$^1$ is alkyl;

R$^2$ is hydrogen or alkyl;

R$^3$ is hydrogen;

R$^6$ is phenyl, substituted phenyl, heteroaryl or substituted heteroaryl;

R$^7$ is phenyl or substituted phenyl;

R$^8$ is phenyl or substituted phenyl;

X is hydrogen or halogen; and

Y is hydrogen or halogen;

or a pharmaceutical salt or stereoisomer thereof.

2. The compound in claim 1 wherein n is 1.

3. The compound in claim 1 wherein A is alanine, leucine or valine.

4. The compound in claim 1 wherein B is halomethyl.

5. The compound in claim 4 wherein B is fluoromethyl.

6. The compound in claim 1 wherein $R^6$ is substituted phenyl.

7. The compound in claim 6 wherein $R^6$ is tetra(halo) phenyl.

8. The compound in claim 7 wherein $R^6$ is tetrafluorophenyl.

9. The compound in claim 8 wherein $R^6$ is 2,3,5,6-tetrafluorophenyl.

10. The compound in claim 1 wherein $R^6$ is heteroaryl or substituted heteroaryl.

11. The compound in claim 10 wherein $R^6$ is phenyl (halomethyl)pyrazol.

12. The compound in claim 11 wherein $R^6$ is 1-phenyl-3-(trifluoromethyl) pyrazol.

13. The compound in claim 1 wherein B is $CH_2OC(=O)R^6$.

14. The compound in claim 13 wherein $R^6$ is substituted phenyl.

15. The compound in claim 14 wherein the substituted phenyl is di(halo)phenyl.

16. The compound in claim 15 wherein the di(halo)phenyl is dichlorophenyl.

17. The compound in claim 16 wherein the dichlorophenyl is 2,6-dichlorophenyl.

18. The compound in claim 11 wherein B is $CH_2OPO(R^7)R^8$.

19. The compound in claim 18 wherein both $R^7$ and $R^8$ are phenyl.

20. The compound in claim 18 wherein both $R^7$ and $R^8$ are substituted phenyl.

21. The compound in claim 1 wherein $R^1$ is methyl.

22. The compound in claim 1 wherein $R^2$ is hydrogen.

23. The compound in claim 1 wherein $R^2$ is alkyl.

24. The compound in claim 23 wherein $R^2$ is methyl.

25. The compound in claim 23 wherein $R^2$ is isobutyl.

26. The compound in claim 1 wherein $R^1$ is alkyl and $R^2$ is hydrogen.

27. The compound in claim 26 wherein $R^1$ is methyl and $R^2$ is hydrogen.

28. The compound in claim 1 wherein both $R^1$ and $R^2$ are alkyl.

29. The compound in claim 28 wherein both $R^1$ and $R^2$ are methyl.

30. The compound in claim 28 wherein $R^1$ is methyl and $R^2$ is isobutyl.

31. The compound in claim 1 wherein X is hydrogen.

32. The compound in claim 1 wherein X is halogen.

33. The compound in claim 32 wherein X is fluorine.

34. The compound in claim 1 wherein Y is hydrogen.

35. The compound in claim 1 wherein Y is halogen.

36. The compound in claim 35 wherein Y is fluorine.

37. The compound in claim 1 wherein X is hydrogen and Y is halogen or X is halogen and Y is hydrogen.

38. The compound in claim 1 wherein both X and Y are hydrogen atoms.

39. The compound in claim 1 wherein both X and Y are halogen.

40. The compound in claim 39 wherein both X and Y are fluorine.

41. A composition comprising the compound of claim 1 and a pharmaceutically acceptable carrier.

* * * * *